United States Patent
Zhang et al.

(10) Patent No.: US 12,226,381 B2
(45) Date of Patent: Feb. 18, 2025

(54) COMPOSITION OF FUSED TRICYCLIC GAMMA-AMINO ACID DERIVATIVES AND THE PREPARATION THEREOF

(71) Applicant: SICHUAN HAISCO PHARMACEUTICAL CO., LTD., Sichuan (CN)

(72) Inventors: Xuanmiao Zhang, Sichuan (CN); Feng Peng, Sichuan (CN); Hua Mao, Sichuan (CN); Juanjuan Deng, Sichuan (CN); Pangke Yan, Sichuan (CN)

(73) Assignee: SICHUAN HAISCO PHARMACEUTICAL CO., LTD., Sichuan (CN)

( * ) Notice: Subject to any disclaimer, the term of this patent is extended or adjusted under 35 U.S.C. 154(b) by 966 days.

(21) Appl. No.: 17/259,757

(22) PCT Filed: Jul. 12, 2019

(86) PCT No.: PCT/CN2019/095856
§ 371 (c)(1),
(2) Date: Jan. 12, 2021

(87) PCT Pub. No.: WO2020/011257
PCT Pub. Date: Jan. 16, 2020

(65) Prior Publication Data
US 2021/0186909 A1 Jun. 24, 2021

(30) Foreign Application Priority Data
Jul. 12, 2018 (CN) .......................... 201810756863.X

(51) Int. Cl.
| | |
|---|---|
| A61K 31/195 | (2006.01) |
| A61K 9/00 | (2006.01) |
| A61K 9/16 | (2006.01) |
| A61K 9/20 | (2006.01) |
| A61K 9/48 | (2006.01) |
| A61P 29/00 | (2006.01) |

(52) U.S. Cl.
CPC .......... *A61K 31/195* (2013.01); *A61K 9/0053* (2013.01); *A61K 9/1694* (2013.01); *A61K 9/2009* (2013.01); *A61K 9/2013* (2013.01); *A61K 9/2018* (2013.01); *A61K 9/2027* (2013.01); *A61K 9/2054* (2013.01); *A61K 9/2095* (2013.01); *A61K 9/4833* (2013.01); *A61K 9/485* (2013.01); *A61K 9/4858* (2013.01); *A61K 9/4866* (2013.01); *A61P 29/00* (2018.01)

(58) Field of Classification Search
CPC .. A61K 31/195; A61K 9/0053; A61K 9/1694; A61K 9/2009; A61K 9/2013; A61K 9/2018; A61K 9/2027; A61K 9/2054; A61K 9/2095; A61K 9/4833; A61K 9/485; A61K 9/4858; A61K 9/4866; A61P 29/00; A61P 25/04; A61P 25/06
See application file for complete search history.

(56) References Cited

U.S. PATENT DOCUMENTS

| | | | |
|---|---|---|---|
| 7,947,738 B2 | 5/2011 | Shimada et al. | |
| 7,998,505 B2 * | 8/2011 | Thoorens | A61K 9/1652 |
| | | | 424/499 |
| 2019/0218172 A1 | 7/2019 | Li et al. | |
| 2021/0186909 A1 | 6/2021 | Zhang et al. | |

FOREIGN PATENT DOCUMENTS

| | | | |
|---|---|---|---|
| AU | 2019302611 B2 | 1/2020 | |
| CA | 3035121 A1 | 3/2018 | |
| CN | 1827095 A | 9/2006 | |
| EA | 000804 B1 | 4/2000 | |
| EP | 3822252 A1 | 5/2021 | |
| KR | 20170115332 A * | 10/2017 | ........... A61K 9/2054 |

(Continued)

OTHER PUBLICATIONS

Nair, A. B. et al. "A simple practice guide for dose conversion between animals and human." Journal of basic and clinical pharmacy vol. 7,2 (2016): 27-31. (Year: 2016).*
Universal Preserv-A-Chem Inc. "Microcrystalline cellulose 102", webpage, Jun. 20, 2016. Retrieved from Internet Archive Wayback Machine <https://whttps://web.archive.org/web/20160620215428/ https://www.upichem.com/products/microcrystalline-cellulose-102/> on Jul. 11, 2024. (Year: 2016).*
Office Action issued in Canadian Application No. 3,106,382; dated Mar. 9, 2022; 5 pages.
Office Action issued in Japanese Patent Application No. 2021-500627; dated Feb. 9, 2022; 8 pages.

(Continued)

*Primary Examiner* — Jean P Cornet
*Assistant Examiner* — Chihyi Lee
(74) *Attorney, Agent, or Firm* — Meunier Carlin & Curfman LLC

(57) ABSTRACT

The present disclosure provides a pharmaceutical composition of fused tricyclic gamma-amino acid derivatives and the use thereof. The pharmaceutical composition includes: (i) a compound having a structure represented by formula (I) or a pharmaceutically acceptable salt thereof, as an active material, in an amount of 1% to 45% by weight; (ii) optionally one or more fillers in an amount of 50% to 95% by weight; (iii) optionally one or more lubricating agents in an amount of 0.1% to 5.5% by weight; and the sum of weight percentages of the all components is 100%, wherein the pharmaceutically acceptable salt of the compound of formula (I) has a structure as follows:

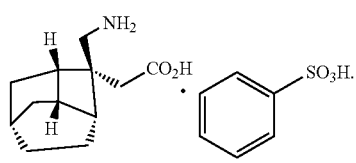

11 Claims, 3 Drawing Sheets

(56) References Cited

FOREIGN PATENT DOCUMENTS

| TW | 201811733 A | 4/2018 |
|---|---|---|
| WO | 9921824 A1 | 5/1999 |
| WO | 02085839 A1 | 10/2002 |
| WO | 2004031124 | 4/2004 |
| WO | 2010079668 | 7/2010 |
| WO | 2017114225 | 7/2017 |
| WO | 2018050046 A1 | 3/2018 |

OTHER PUBLICATIONS

Office Action issued in AU Application No. 2019302611; dated Aug. 16, 2021; 3 pages.
Search Report issued in BR Application No. BR112021000398-3; 6 pages; dated Apr. 11, 2023.
Office Action issued in EA application No. 202190126/28; 4 pages; dated Apr. 7, 2023.
Office Action issued in CN Application No. 201980045729.1; dated Nov. 1, 2022.; 12 pages.
Search Report issued in CN Application No. 201980045729.1; dated Nov. 1, 2022; 4 pages.
Felix, R. et al. "Dissection of Functional Domains of the Voltage-Dependent Ca2+ Channel a2d Subunit", The Journal of Neuroscience, Sep. 15, 1997, 17(18):6884-6891.
Hobom, M. et al. "Neuronal distribution and functional characterization of the calcium channel a2s-2 subunit", European Journal of Neuroscience, vol. 12, pp. 1217-1226, 2000.
Klugbauer, N. et al. "Molecular Diversity of the Calcium Channel a2d Subunit", The Journal of Neuroscience, Jan. 15, 1999, 19(2):684-691.
Qin, N. et al. "Molecular Cloning and Characterization of the Human Voltage-Gated Calcium Channel a2s-4 Subunit", Mol Pharmacol 62:485-496, 2002.
Extended European Search Report issued in EP Application No. 19833773.5; dated Oct. 15, 2021; 10 pages.
Office Action issued in CN Application No. 201980045729.1; dated Jun. 29, 2023; 8 pages.
Office Action issued in MX Application No. MX/a/2021/000403; dated Jun. 29, 2023; 9 pages.
Office Action issued in MY Applicaiton No. PI2021000159; dated Jun. 22, 2023; 4 pages.
First Office Action issued on Aug. 1, 2022 for counterpart Korean patent application No. 10-2021-7003520.
Second Office Action and Search Report issued on Aug. 11, 2022 for counterpart Taiwan patent application No. 108124713.
Second Office Action issued for corresponding Japanese Patent Application 2021-500627 mailed on Sep. 6, 2022.
Office Action issued in IN application No. 202127003904; dated Nov. 11, 2021; 5 pages.
International Search Report (English) and Written Opinion dated Oct. 15, 2019, from International Application No. PCT/CN2019/095856, 16 pages.
Office Action issued in TW Application No. 108124713; dated Feb. 23, 2021; 5 pages.
Search Report issued in TW Application No. 108124713; dated Feb. 24, 2021; 1 page.
Rowe et al.; "Handbook of Pharmaceutical Excipients. Sixth edition"; Pharmaceutical Press AM) American Pharmacists Association, USA; dated Feb. 25, 2009; 20 pages.
Shanmugam Srinivasan. "Granulation techniques and technologies: recent progresses"; Bioimpacts; vol. 5, No. 1, p. 55-63; dated Feb. 18, 2015; 9 pages.
Office Action issued in EA Application No. 202190126/28; dated Sep. 14, 2022; 13 pages.
Office Action issued in KR Application No. 10-2021-7003520; dated Nov. 1, 2022; 6 pages.
Office Action issued in EP application No. 19833773.5-1109; dated Dec. 19, 2023; 6 pages.
Office Action issued in MX application No. MX/a/2021/000403; dated Dec. 13, 2023; 11 pages.

* cited by examiner

COMPOSITION OF FUSED TRICYCLIC GAMMA-AMINO ACID DERIVATIVES AND THE PREPARATION THEREOF

TECHNICAL FIELD

The present disclosure relates to a field of medication, in particular, to a pharmaceutical composition of fused tricyclic gamma-amino acid derivatives and the use thereof.

BACKGROUND

Diabetic peripheral neuralgic pain (DPNP) is a common chronic complication of diabetes. At least 25% of diabetic patients suffered from painful diabetic peripheral neuropathy, and 50% of diabetic patients with a disease history of more than 25 years will develop into neuralgia. Currently, there are more than 10 million DPNP patients in China.

Post herpetic neuralgia (PHN) is the most common complication of herpes zoster. The annual incidence of herpes zoster is about 3-5%, and about 9-34% of patients with herpes zoster will develop into PHN. The incidence of herpes zoster tends to increase with age. About 65% of patients with herpes zoster, aged 60 and above, will develop into PHN, while the number is up to 75% in those aged 70 and above. There is a lack of relevant research data in China. However, according to the above data, it is estimated that there are about 4 million PHN patients in China.

Fibromyalgia syndrome (FMs) is a group of clinical syndromes of unknown etiology and characterized by systemic pain and significant physical discomfort. The overall prevalence of FMs is 2.7% in the world, with 2% in the United States and 0.8% in China.

At present, drugs for symptomatic treatment of peripheral neuralgia mainly comprise anticonvulsants, tricyclic antidepressants, opioid analgesics, local analgesics and the like.

The therapeutic agents approved by FDA include voltage-dependent calcium channel antagonists such as pregabalin, gabapentin, 5-HT/NE reuptake inhibitors such as duloxetine, milnacipran, µ-opioid receptor agonist/NE reuptake inhibitor such as tapentadol, and the topical external-use drugs such as lidocaine patch, capsaicin patch. At present, only pregabalin and gabapentin are approved for PHN treatment by CFDA, while no drug has been approved for treating DPNP and FMs.

Voltage-gated calcium channels are composed of al subunit and accessory protein $\alpha2\delta$-, $\beta$-, $\gamma$-subunits. $\alpha2\delta$ protein can adjust the density of calcium channel and the calcium-channel voltage-dependent dynamics (Felix et al (1997) J. Neuroscience 17: 6884-6891; Klugbauer et al (1999) J. Neuroscience 19: 684-691; Hobom et al (2000) Eur. J. Neuroscience 12: 1217-1226; and Qin et al (2002) Mol. Pharmacol. 62: 485-496). It has been demonstrated that compounds that exhibit high affinity binding to the voltage-dependent calcium-channel subunit $\alpha2\delta$ are effective in the treatment of pain, such as pregabalin and gabapentin. In mammals, the $\alpha2\delta$ protein has 4 subtypes, each of which is encoded by a different gene. The subtype 1 and subtype 2 of $\alpha2\delta$ show high affinity with pregabalin, while the subtype 3 and subtype 4 of $\alpha2\delta$ have no significant drug-binding capacity.

Clinically, pregabalin is administrated three times a day or twice a day, with a low clinical compliance to patients. Pregabalin only has an alleviation effect on pain in about 30-50% of patients, and has poor effects on refractory DPNP and the like. The side effects such as dizziness, drowsiness, weight gain, edema and the like occur in a high rate in the clinical use, which may affect the life quality of patients.

SUMMARY OF THE DISCLOSURE

According to the present disclosure, there is provided a pharmaceutical composition of a fused tricyclic gamma-amino acid derivative, having a novel structure and a good potency, or a pharmaceutically acceptable salt thereof and the use thereof in the field of analgesia.

According to the present disclosure, there is also provided a method of treating and/or preventing pain, comprising administering an effective amount of a fused tricyclic gamma-amino acid derivative or a pharmaceutically acceptable salt thereof.

The novel compound of a fused tricyclic gamma-amino acid derivative (of formula (I) structure or a pharmaceutically acceptable salt thereof) provided in the present disclosure is a calcium-ion-channel $\alpha2\delta$ antagonist, which can competitively bind to a calcium-ion-channel $\alpha2\delta$ subunit. The compound is associated with the endogenous inhibitory neurotransmitter, GABA, which is associated with the regulation of brain neuron activity, has a therapeutic effect on peripheral neuralgia caused by diabetes, post herpetic neuralgia and fibromyalgia, and thus is expected to overcome the defect of pregabalin.

According to the present disclosure, there is provided a pharmaceutical composition comprising a compound represented by formula (I) as below or a pharmaceutically acceptable salt thereof:

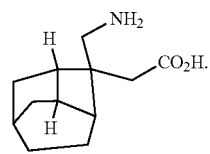

(I)

According to the present disclosure, there is provided a pharmaceutical composition comprising a compound represented by formula (I) or a pharmaceutically acceptable salt thereof, wherein formula (I) is formula (II) as below:

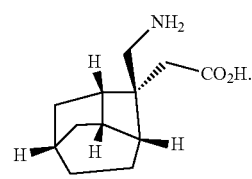

(II)

In an embodiment, optionally, the compound represented by formula (I) or (II) or a pharmaceutically acceptable salt thereof is included in an amount of 1-100 mg.

Optionally, the compound represented by formula (I) or (II) or a pharmaceutically acceptable salt thereof is included in an amount of 2-80 mg.

Optionally, the compound represented by formula (I) or (II) or a pharmaceutically acceptable salt thereof is included in an amount of 2-60 mg.

Optionally, the compound represented by formula (II) or a pharmaceutically acceptable salt thereof is included in an amount of 2-50 mg.

Optionally, the compound represented by formula (I) or (II) or a pharmaceutically acceptable salt thereof is included in an amount of 5-50 mg.

Optionally, the compound represented by formula (I) or (II) or a pharmaceutically acceptable salt thereof is included in an amount of 5-40 mg.

Optionally, the compound represented by formula (I) or (II) or a pharmaceutically acceptable salt thereof is included in an amount of 5-30 mg.

Optionally, the compound represented by formula (I) or (II) or a pharmaceutically acceptable salt thereof is included in an amount of 5-20 mg.

Optionally, the compound represented by formula (I) or (II) or a pharmaceutically acceptable salt thereof is included in an amount of 5-10 mg.

Optionally, the compound represented by formula (I) or (II) or a pharmaceutically acceptable salt thereof is included in an amount of 10-80 mg.

Optionally, the compound represented by formula (I) or (II) or a pharmaceutically acceptable salt thereof is included in an amount of 10-60 mg.

Optionally, the compound represented by formula (I) or (II) or a pharmaceutically acceptable salt thereof is included in an amount of 10-50 mg.

Optionally, the compound represented by formula (I) or (II) or a pharmaceutically acceptable salt thereof is included in an amount of 20-80 mg.

Optionally, the compound represented by formula (I) or (II) or a pharmaceutically acceptable salt thereof is included in an amount of 20-60 mg.

Optionally, the compound represented by formula (I) or (II) or a pharmaceutically acceptable salt thereof is included in an amount of 20-50 mg.

Optionally, the compound represented by formula (I) or (II) or a pharmaceutically acceptable salt thereof is included in an amount of 30-50 mg.

In a specific embodiment, the compound represented by formula (I) or (II) or a pharmaceutically acceptable salt thereof is included in an amount of 5 mg, 10 mg, 15 mg, 20 mg, 25 mg, 30 mg, 35 mg, 40 mg, 45 mg or 50 mg.

In any one of the aforesaid embodiments, the pharmaceutically acceptable salt is selected from a benzene sulfonate.

There is also provided a method of treating and/or preventing pain, comprising administering an effective amount of the compound represented by formula (I) or (II) or a pharmaceutically acceptable salt thereof, wherein the effective amount ranges optionally from 1 to 100 mg, or from 2 to 80 mg, or from 2 to 60 mg, or from 2 to 50 mg, or from 5 to 50 mg, or from 5 to 40 mg, or from 5 to 30 mg, or from 5 to 20 mg, or from 10 to 80 mg, or from 10 to 70 mg, or from 10 to 60 mg, or from 10 to 50 mg, or from 10 to 45 mg, or from 15 to 70 mg, or from 15 to 60 mg, or from 15 to 50 mg, or from 15 to 45 mg, or from 20 to 70 mg, or from 20 to 60 mg, or from 20 to 50 mg, or from 20 to 45 mg.

Preferably, the compound represented by formula (I) or (II) or a pharmaceutically acceptable salt thereof is a benzene sulfonate thereof.

When the pharmaceutically acceptable salt is administered as an active ingredient, the effective dose is a value converted to a free base.

In one variation, it is administered orally.

In one variation, the pain comprises: postherpetic neuralgia, trigeminal neuralgia, migraine, pain associated with osteoarthritis or arthrorheumatism, lower back pain, sciatica, dental pain, pain caused by burns, pain caused by diabetic neuropathy, pain caused by chemotherapy-induced neuropathy, HIV-associated neuralgia, AIDS-associated neuralgia, cancer-associated neuralgia or non-neuropathic pain, acute or chronic tension headache, postoperative pain or fibromyalgia. In a particular variation, the pain comprises: postherpetic neuralgia, pain caused by diabetic neuropathy, or fibromyalgia.

There is also provided the use of the aforesaid pharmaceutical composition in the preparation of a medication for treating and/or preventing pain. Preferably, the pain comprises: postherpetic neuralgia, trigeminal neuralgia, migraine, pain associated with osteoarthritis or arthrorheumatism, lower back pain, sciatica, dental pain, pain caused by burns, pain caused by diabetic neuropathy, pain caused by chemotherapy-induced neuropathy, HIV-associated neuralgia, AIDS-associated neuralgia, cancer-associated neuralgia or non-neuropathic pain, acute or chronic tension headache, postoperative pain or fibromyalgia.

There is also provided the use of the compound represented by formula (I) or (II) or a pharmaceutically acceptable salt thereof in the preparation of a medication for treating and/or preventing pain.

In an embodiment, optionally, the compound represented by formula (I) or (II) or a pharmaceutically acceptable salt thereof is administrated in a single dose of 1-100 mg.

Optionally, the compound represented by formula (I) or (II) or a pharmaceutically acceptable salt thereof is administrated in a single dose of 2-80 mg.

Optionally, the compound represented by formula (I) or (II) or a pharmaceutically acceptable salt thereof is administrated in a single dose of 2-60 mg.

Optionally, the compound represented by formula (I) or (II) or a pharmaceutically acceptable salt thereof is administrated in a single dose of 2-50 mg.

Optionally, the compound represented by formula (I) or (II) or a pharmaceutically acceptable salt thereof is administrated in a single dose of 5-50 mg.

Optionally, the compound represented by formula (I) or (II) or a pharmaceutically acceptable salt thereof is administrated in a single dose of 5-40 mg.

Optionally, the compound represented by formula (I) or (II) or a pharmaceutically acceptable salt thereof is administrated in a single dose of 5-30 mg.

Optionally, the compound represented by formula (I) or (II) or a pharmaceutically acceptable salt thereof is administrated in a single dose of 5-20 mg.

Optionally, the compound represented by formula (I) or (II) or a pharmaceutically acceptable salt thereof is administrated in a single dose of 5-10 mg.

Optionally, the compound represented by formula (I) or (II) or a pharmaceutically acceptable salt thereof is administrated in a single dose of 10-80 mg.

Optionally, the compound represented by formula (I) or (II) or a pharmaceutically acceptable salt thereof is administrated in a single dose of 10-60 mg.

Optionally, the compound represented by formula (I) or (II) or a pharmaceutically acceptable salt thereof is administrated in a single dose of 10-50 mg.

Optionally, the compound represented by formula (I) or (II) or a pharmaceutically acceptable salt thereof is administrated in a single dose of 20-80 mg.

Optionally, the compound represented by formula (I) or (II) or a pharmaceutically acceptable salt thereof is administrated in a single dose of 20-60 mg.

Optionally, the compound represented by formula (I) or (II) or a pharmaceutically acceptable salt thereof is administrated in a single dose of 20-50 mg.

Optionally, the compound represented by formula (I) or (II) or a pharmaceutically acceptable salt thereof is administrated in a single dose of 30-50 mg.

In a specific embodiment, the compound represented by formula (I) or (II) or a pharmaceutically acceptable salt thereof is included in an amount of 5 mg, 10 mg, 15 mg, 20 mg, 25 mg, 30 mg, 35 mg, 40 mg, 45 mg or 50 mg.

In each of the above embodiments or variations about the use, the pharmaceutically acceptable salt is selected from benzene sulfonates.

In each of the above embodiments or variation of the use, when the pharmaceutically acceptable salt of the compound represented by formula (I) or (II) is used in the preparation of the medication for treating and/or preventing pain, the single dose is a value converted to a free base.

Another object of the present disclosure is to improve the stability of the formulation and to solve the problem of content uniformity in the production of the formulation, thereby obtaining a formulation having a qualified content uniformity and a good chemical stability. According to the present disclosure, there is provided a formulation containing the compound of formula (I) or formula (II) as an active ingredient, which can be in a form of tablets, capsules, granules and the like.

The formulation, as provided by the present disclosure, is quick in dissolution, and good in chemical stability, safe, effective and few in side effects.

According to the present disclosure, there is provided a pharmaceutical composition, which, based on the total weight of the pharmaceutical composition (100%), comprises:
(i) an active material having a structure as represented by formula (I) or formula (II) or a pharmaceutically acceptable salt thereof in an amount of 1% to 45% by weight, or in an amount of 1% to 40% by weight in some embodiments, or in an amount of 1% to 35% by weight in some embodiments, or in an amount of 1% to 30% by weight in some embodiments, or in an amount of 1% to 25% by weight in some embodiments, or in an amount of 5% to 45% by weight in some embodiments, or in an amount of 5% to 40% by weight in some embodiments, or in an amount of 5% to 35% by weight in some embodiments, or in an amount of 5% to 30% by weight in some embodiments, or in an amount of 5% to 25% by weight in some embodiments, or in an amount of 5% to 21% by weight in some embodiments;
(ii) optionally one or more filler in an amount of 50% to 95% by weight, or in an amount of 55% to 94% by weight in some embodiments, or in an amount of 79% to 94% by weight in some embodiments;
(iii) optionally one or more lubricating agents in an amount of 0.1% to 6% by weight, or in an amount of 0.1% to 5.5% by weight in some embodiments, or in an amount of 0.1% to 2% by weight in some embodiments, or in an amount of 0.1% to 1.5% by weight in some embodiments, or in an amount of 0.5% to 1.5% by weight in some embodiments, or in an amount of 0.5% to 1% by weight in some embodiments, or in an amount of 0.5% to 0.9% by weight in some embodiments, or in an amount of 0.5% to 0.8% by weight in some embodiments, or in an amount of 0.5% to 0.7% by weight in some embodiments, or in an amount of 0.5% to 0.6% by weight in some embodiments;
wherein the above ranges may be arbitrarily combined, provided that the sum of weight percents of the all components is 100%; and wherein the structure of formula (I) is as follows:

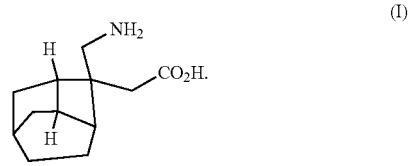 [SMILES: NCC1(CC(=O)O)C2CCC3CC2C1C3]

(I)

The pharmaceutical composition according to the present disclosure, wherein the structure of formula (I) is as follows:

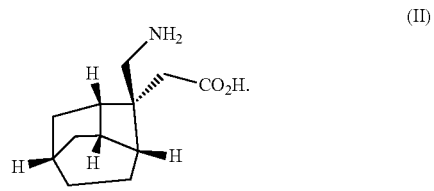 [SMILES: NC[C@@]1(CC(=O)O)[C@@H]2CC[C@H]3C[C@@H]2[C@@H]1C3]

(II)

The pharmaceutical composition according to the present disclosure, wherein the pharmaceutically acceptable salt of the compound of formula (I) has a structure as follows:

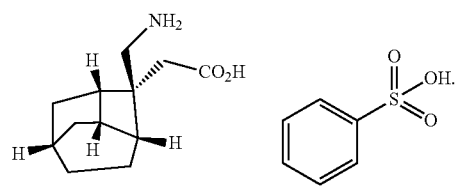 [SMILES: NC[C@@]1(CC(=O)O)[C@@H]2CC[C@H]3C[C@@H]2[C@@H]1C3 ; O=S(=O)(O)c1ccccc1]

The pharmaceutically acceptable salt of the compound of formula (I) has a structure in a crystal form, and has characteristic diffraction peaks in the 2θ angles of 9.72°±0.2°, 14.00°±0.2°, 16.33°±0.2°, 19.32°±0.2°, 20.46°±0.2°, 21.69°±0.2° and 25.33°±0.2° in the X-ray powder-diffraction spectrum using Cu-Kα for radiation. It further has characteristic diffraction peaks in the 2θ angles of 11.21±0.20, 15.16°±0.2°, 18.870±0.20, 19.880±0.20, 23.470±0.20 and 27.960±0.20 in the X-ray powder-diffraction spectrum using Cu-Kα for radiation. It further has characteristic diffraction peaks in the 2θ angles of 21.30°±0.2°, 25.40°±0.2°, 29.82°±0.2° in the X-ray powder-diffraction spectrum. Further, the crystal of the pharmaceutically acceptable salt of the compound of formula (I) has an X-ray powder-diffraction spectrum, using Cu-Kα for radiation, as shown in FIG. 4. Further, the TGA/DSC spectrum of the crystal of the pharmaceutically acceptable salt of the compound of formula (I) is shown in FIG. 5. Moreover, the pharmaceutically acceptable salt of the compound of formula (I) has a single-crystal diffraction spectrum as shown in FIG. 6, wherein the pharmaceutically acceptable salt of the compound of formula (I) has a structure as follows:

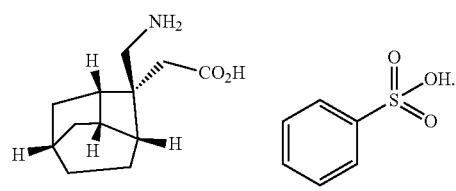 [SMILES: NC[C@@]1(CC(=O)O)[C@@H]2CC[C@H]3C[C@@H]2[C@@H]1C3 ; O=S(=O)(O)c1ccccc1]

The composition according to the present disclosure may be a pharmaceutical formulation in a form of tablets, granules, microcapsules, pills or capsules. It is in a form of tablets or capsules in certain embodiments. Further, it is in a form of capsules in certain embodiments.

The composition according to the present disclosure includes the active material in an amount of 1% to 45% by weight, or in an amount of 1% to 40% by weight in certain embodiments, or in an amount of 1% to 35% by weight in certain embodiments, or in an amount of 1% to 30% by weight in certain embodiments, or in an amount of 1% to 25% by weight in certain embodiments, or in an amount of 5% to 45% by weight in certain embodiments, or in an amount of 5% to 40% by weight in certain embodiments, or in an amount of 5% to 35% by weight in certain embodiments, or in an amount of 5% to 30% by weight in certain embodiments, or in an amount of 5% to 25% by weight in certain embodiments, or in an amount of 5% to 21% by weight in certain embodiments, or in an amount of 5.5% to 21% by weight in certain embodiments, or in an amount of 5.5% to 20.5% by weight in certain embodiments, or in an amount of 5.5% to 20% by weight in certain embodiments.

The filler in the composition of the present disclosure is one or more selected from mannitol, low-substituted hydroxypropyl cellulose and microcrystalline cellulose. In certain embodiments, the filler is selected from one or more of mannitol and microcrystalline cellulose. In certain embodiments, it is a combination of mannitol and microcrystalline cellulose.

The filler in the composition of the present disclosure is selected from a combination of mannitol and microcrystalline cellulose with a content of mannitol of 9% to 40% by weight. In certain embodiments, the content of mannitol is 9% to 35% by weight; in certain embodiments, the content of mannitol is 10% to 28% by weight; in certain embodiments, the content of mannitol is 9% to 25% by weight; in certain embodiments, the content of mannitol is 9% to 20% by weight; in certain embodiments, the content of mannitol is 15% to 35% by weight; in certain embodiments, the content of mannitol is 15% to 30% by weight; in certain embodiments, the content of mannitol is 15% to 28% by weight; in certain embodiments, the content of mannitol is 15% to 25% by weight; in certain embodiments, the content of mannitol is 15% to 20% by weight.

The filler in the composition according to the present disclosure is selected from a combination of mannitol and microcrystalline cellulose, wherein said microcrystalline cellulose comprises microcrystalline cellulose A and microcrystalline cellulose B. The microcrystalline cellulose A is selected from microcrystalline cellulose PH14, microcrystalline cellulose PH12, microcrystalline cellulose 12 or microcrystalline cellulose 14. In certain embodiments, the microcrystalline cellulose A is selected from microcrystalline cellulose 12; in certain embodiments, the microcrystalline cellulose A is selected from microcrystalline cellulose PH12; in certain embodiments, the microcrystalline cellulose A is selected from microcrystalline cellulose PH14; in certain embodiments, the microcrystalline cellulose A is selected from microcrystalline cellulose 14. The microcrystalline cellulose B is selected from microcrystalline celluloses of PH102, PH105, PH103, PH301, PH101, PH112, PH302, and microcrystalline celluloses of 102, 105, 103, 301, 101, 112, 302. In certain embodiments, the microcrystalline cellulose B is selected from microcrystalline cellulose 102; in certain embodiments, the microcrystalline cellulose B is selected from microcrystalline cellulose PH102.

The filler in the composition according to the present disclosure is selected from a combination of mannitol and microcrystalline cellulose, wherein said microcrystalline cellulose comprises microcrystalline cellulose A and B, which are respectively selected from microcrystalline cellulose 102 and microcrystalline cellulose 12.

The filler in the composition according to the disclosure is selected from a combination of mannitol and microcrystalline cellulose, wherein the microcrystalline cellulose comprises microcrystalline cellulose A and B, with a content of the microcrystalline cellulose A of 3% to 60% by weight. In certain embodiments, the content of the microcrystalline cellulose A is 3% to 59% by weight; in certain embodiments, the content of the microcrystalline cellulose A is 3% to 58% by weight; in certain embodiments, the content of the microcrystalline cellulose A is 3% to 10% by weight; in certain embodiments, the content of the microcrystalline cellulose A is 3% to 8% by weight; in certain embodiments, the content of the microcrystalline cellulose A is 5% to 15% by weight; in certain embodiments, the content of the microcrystalline cellulose A is 5% to 12% by weight; in certain embodiments, the content of the microcrystalline cellulose A is 5% to 10% by weight; in certain embodiments, the content of the microcrystalline cellulose A is 5% to 9% by weight; in certain embodiments, the content of the microcrystalline cellulose A is 5% to 8% by weight; in certain embodiments, the content of the microcrystalline cellulose A is 5% to 7.5% by weight; in certain embodiments, the content of the microcrystalline cellulose A is 5.5% to 7.5% by weight.

The filler in the composition according to the disclosure is selected from a combination of mannitol and microcrystalline cellulose, wherein the microcrystalline cellulose comprises microcrystalline cellulose A and B, with a content of the microcrystalline cellulose B of 17% to 80% by weight. In certain embodiments, the content of the microcrystalline cellulose B is 17% to 72% by weight; in certain embodiments, the content of the microcrystalline cellulose B is 40% to 80% by weight; in certain embodiments, the content of the microcrystalline cellulose B is 40% to 70% by weight; in certain embodiments, the content of the microcrystalline cellulose B is 40% to 75% by weight; in certain embodiments, the content of the microcrystalline cellulose B is 41% to 72% by weight; in certain embodiments, the content of the microcrystalline cellulose B is 42% to 72% by weight; in certain embodiments, the content of the microcrystalline cellulose B is 50% to 80% by weight; in certain embodiments, the content of the microcrystalline cellulose B is 50% to 75% by weight; in certain embodiments, the content of the microcrystalline cellulose B is 50% to 70% by weight; in certain embodiments, the content of the microcrystalline cellulose B is 55% to 80% by weight; in certain embodiments, the content of the microcrystalline cellulose B is 55% to 75% by weight; in certain embodiments, the content of the microcrystalline cellulose B is 56% to 72% by weight; in certain embodiments, the content of the microcrystalline cellulose B is 56% to 61% by weight.

The filler in the composition according to the disclosure is selected from a combination of mannitol and microcrystalline cellulose, wherein the microcrystalline cellulose comprises microcrystalline cellulose A and B, with a content of the microcrystalline cellulose A of 5% to 8% by weight. In certain embodiments, the content of the microcrystalline cellulose A is 5% to 7.5% by weight; in certain embodiments, the content of the microcrystalline cellulose A is 5.5% to 7.5% by weight, and a content of the microcrystalline cellulose B is 55% to 75% by weight. In certain embodiments, the content of the microcrystalline cellulose B is 56% to 72% by weight; in certain embodiments, the content of the microcrystalline cellulose B is 56% to 61% by weight.

The filler in the composition according to the disclosure is selected from a combination of mannitol and microcrystalline cellulose, wherein the microcrystalline cellulose comprises microcrystalline cellulose 12 and microcrystalline cellulose 102, with a content of the microcrystalline cellulose 12 of 5% to 8% by weight. In certain embodiments, the content of the microcrystalline cellulose 12 is 5% to 7.5% by weight; in certain embodiments, the content of the microcrystalline cellulose 12 is 5.5% to 7.5% by weight, and a content of the microcrystalline cellulose 102 is 55% to 75% by weight. In certain embodiments, the content of the microcrystalline cellulose 102 is 56% to 72% by weight; in certain embodiments, the content of the microcrystalline cellulose 102 is 56% to 61% by weight.

The microcrystalline cellulose 12 has a particle size of D50 ranged from 130 μm to 230 μm, and a particle size of D90 ranged from 270 μm to 450 μm. The microcrystalline cellulose 102 has a particle size of D50 ranged from 90 μm to 150 μm, and a particle size of D90 ranged from 190 μm to 300 μm.

The filler in the composition according to the disclosure is selected from a combination of mannitol and microcrystalline cellulose, wherein the microcrystalline cellulose comprises microcrystalline cellulose 12 and microcrystalline cellulose 102, with a content of the microcrystalline cellulose 12 of 5% to 8% by weight. In certain embodiments, the content of the microcrystalline cellulose 12 is 5% to 7.5% by weight; in certain embodiments, the content of the microcrystalline cellulose 12 is 5.5% to 7.5% by weight; and a content of the microcrystalline cellulose 102 of 55% to 75% by weight. In certain embodiments, the content of the microcrystalline cellulose 102 is 56% to 72% by weight; in certain embodiments, the content of the microcrystalline cellulose 102 is 56% to 61% by weight. The microcrystalline cellulose 12 has a particle size of D50 ranged from 130 μm to 230 μm, and a particle size of D90 ranged from 270 μm to 450 μm. The microcrystalline cellulose 102 has a particle size of D50 ranged from 90 μm to 150 μm, and a particle size of D90 ranged from 190 μm to 300 μm.

The filler in the composition according to the present disclosure is selected from a combination of mannitol and microcrystalline cellulose, wherein the content, by weight percent, of the filler in the composition is the sum of that of the microcrystalline cellulose comprising microcrystalline cellulose A, B and that of mannitol, sum of which and that of other ingredients is 100%.

The filler in the composition according to the present disclosure is selected from a combination of mannitol and microcrystalline cellulose, wherein the microcrystalline cellulose has a particle size D50 ranged from 90 μm to 230 μm. When the microcrystalline cellulose has a particle size D50 less than 90 μm, a binder has to be added in the composition.

The lubricating agent in the composition according to the present disclosure is one or more selected from stearic acid, magnesium stearate, sodium stearyl fumarate and glyceryl behenate. In certain embodiments it is selected from magnesium stearate or stearic acid; in certain embodiments, it is magnesium stearate.

The lubricating agent is included in the composition according to the present disclosure in amount of 0.5% to 6% by weight, or in an amount of 0.5% to 5.5% by weight in some embodiments, or in an amount of 0.5% to 5.3% by weight in some embodiments, or in an amount of 0.5% to 2% by weight in some embodiments, or in an amount of 0.5% to 1.5% by weight in some embodiments, or in an amount of 0.5% to 1% by weight in some embodiments, or in an amount of 0.5% to 0.9% by weight in some embodiments, or in an amount of 0.5% to 0.8% by weight in some embodiments, or in an amount of 0.5% to 0.7% by weight in some embodiments, or in an amount of 0.5% to 0.6% by weight in some embodiments, or in an amount of 0.55% to 0.6% by weight in some embodiments, or in an amount of 0.51% to 0.55% by weight in some embodiments.

The composition according to the present disclosure may further include, optionally, one or more binders, if necessary.

The binder may be selected from hydroxypropyl cellulose or povidone.

The binder is included in an amount of 1% to 10% by weight, or in an amount of 1% to 6% in some embodiments, or in an amount of 1% to 5% in some embodiments, or in an amount of 1% to 4% in some embodiments, or in an amount of 1% to 3% in some embodiments, or in an amount of 4% in some embodiments, or in an amount of 3% in some embodiments.

The composition according to the present disclosure may further include, optionally, one or more disintegrating agents, if necessary.

The disintegrating agent may be selected from croscarmellose sodium and sodium carboxymethyl starch.

The disintegrating agent is included in an amount of 1% to 10% by weight, or in an amount of 1% to 5% in some embodiments, or in an amount of 1% to 4% in some embodiments, or in an amount of 3% to 4% in some embodiments, or in an amount of 4% in some embodiments.

The composition according to the present disclosure may further include, optionally, one or more glidants, if necessary.

The glidant is selected from silica or talc.

The glidant is included in an amount of 1% to 10% by weight, or in an amount of 1% to 6% in some embodiments, or in an amount of 1% to 5% in some embodiments, or in an amount of 1% to 4% in some embodiments, or in an amount of 1% to 3% in some embodiments, or in an amount of 4% in some embodiments, or in an amount of 3% in some embodiments.

The above percentages are based on the total weight of the composition (100%), while the defined percentage ranges of any individual component may be arbitrarily combined with that of the other component(s), provided the total percentage thereof is 100%.

The composition according to the present disclosure is a capsule formulation comprising:
  (i) a pharmaceutically acceptable salt of the compound of formula (I), as an active material, which is included in an amount of 1% to 45% by weight, or in an amount of 1% to 40% by weight in some embodiments, or in an amount of 1% to 35% by weight in some embodiments, or in an amount of 1% to 30% by weight in some embodiments, or in an amount of 1% to 25% by weight in some embodiments, or in an amount of 5% to 45% by weight in some embodiments, or in an amount of 5% to 40% by weight in some embodiments, or in an amount of 5% to 35% by weight in some embodiments, or in an amount of 5% to 30% by weight in some embodiments, or in an amount of 5% to 25% by weight in some embodiments, or in an amount of 5% to 21% by weight in some embodiments, or in an amount of 5.5% to 21% by weight in some embodiments, or in an amount of 5.5% to 20.5% by weight in some embodiments, or in an amount of 5.5% to 20% by weight in some embodiment;
(ii) a filler comprising mannitol, microcrystalline cellulose A and microcrystalline cellulose B, wherein mannitol is included in an amount of 9% to 40% by weight, or in an amount of 9% to 35% by weight in some embodiments, or in an amount of 10% to 28% by weight in some embodiments, or in an amount of 9% to 25% by weight in some embodiments, or in an amount of 9% to 20% by weight in some embodiments, or in an amount of 15% to 35% by weight in some embodiments, or in an amount of 15% to 30% by weight in some embodiments, or in an amount of 15% to 28% by weight in some embodiments, or in an amount of 15% to 25% by weight in some embodiments, or in an amount of 15% to 20% by weight in some embodiment; the microcrystalline cellulose A is included in an amount of 3% to 60% by weight, or in an amount of 3% to 59% by weight in some embodiments, or in an amount of 3% to 58% by weight in some embodiments, or in an amount of 3% to 10% by weight in some embodiments, or in an amount of 3% to 8% by weight in some embodiments, or in an amount of 5% to 15% by weight in some embodiments, or in an amount of 5% to 12% by weight in some embodiments, or in an amount of 5% to 10% by weight in some embodiments, or in an amount of 5% to 9% by weight in some embodiments, or in an amount of 5% to 8% by weight in some embodiments, or in an amount of 5% to 7.5% by weight in some embodiments, or in an amount of 5.5% to 7.5% by weight in some embodiment; and the microcrystalline cellulose B is included in an amount of 17% to 80% by weight, or in an amount of 40% to 80% by weight in some embodiments, or in an amount of 40% to 70% by weight in some embodiments, or in an amount of 40% to 75% by weight in some embodiments, or in an amount of 41% to 72% by weight in some embodiments, or in an amount of 42% to 72% by weight in some embodiments, or in an amount of 50% to 80% by weight in some embodiments, or in an amount of 50% to 75% by weight in some embodiments, or in an amount of 50% to 70% by weight in some embodiments, or in an amount of 55% to 80% by weight in some embodiments, or in an amount of 55% to 75% by weight in some embodiments, or in an amount of 56% to 72% by weight in some embodiments, or in an amount of 56% to 61% by weight in some embodiment;
(iii) magnesium stearate, as a lubricating agent, which is included in an amount of 0.5% to 6% by weight, or in an amount of 0.5% to 5.5% by weight in some embodiments, or in an amount of 0.5% to 5.3% by weight in some embodiments, or in an amount of 0.5% to 2% by weight in some embodiments, or in an amount of 0.5% to 1.5% by weight in some embodiments, or in an amount of 0.5% to 1% by weight in some embodiments, or in an amount of 0.5% to 0.9% by weight in some embodiments, or in an amount of 0.5% to 0.8% by weight in some embodiments, or in an amount of 0.5% to 0.7% by weight in some embodiments, or in an amount of 0.5% to 0.6% by weight in some embodiments, or in an amount of 0.55% to 0.6% by weight in some embodiments, or in an amount of 0.51% to 0.55% by weight in some embodiments;

wherein the defined percentage ranges of any individual component may be arbitrarily combined with that of the other component(s), provided the total percentage of all components is 100%; and wherein the pharmaceutically acceptable salt of the compound of formula (I) has a structure as follows:

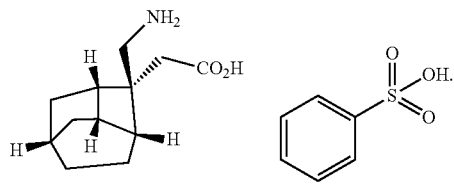 [SMILES: NC[C@@]1(CC(=O)O)[C@@H]2CC[C@H]3C[C@@H]2[C@@H]1C3 ; O=S(=O)(O)c1ccccc1]

The composition according to the present disclosure may further comprise a glidant, which is selected from silica and talc. In some embodiments, it is silica.

The compositions according to the present disclosure may further comprise a binder selected from hydroxypropyl cellulose or povidone. In certain embodiments, the binder is hydroxypropyl cellulose. In particular, when the composition only comprises one auxiliary material as the filler, the composition further comprises a binder.

The present disclosure also relates to a pharmaceutical composition in a form of tablets, comprising:
(i) a pharmaceutically acceptable salt of the compound of formula (I), as an active material which is included in an amount of 4% to 35% by weight, or in an amount of 4% by weight in some embodiments, or in an amount of 11% by weight in some embodiments, or in an amount of 20% by weight in some embodiments, or in an amount of 34% by weight in some embodiments;
(ii) a filler comprising mannitol and microcrystalline cellulose B, wherein mannitol is included in an amount of 13% to 60% by weight, or in an amount of 13% to 40% by weight in some embodiments, or in an amount of 13% to 20% by weight in some embodiments; and the microcrystalline cellulose B is included in an amount of 10% to 60% by weight, or in an amount of 19% to 60% by weight in some embodiments, or in an amount of 19% to 50% by weight in some embodiments, or in an amount of 19% to 40% by weight in some embodiments, or in an amount of 40% to 60% by weight in some embodiments, or in an amount of 40% to 50% by weight in some embodiments, or in an amount of 50% to 60% by weight in some embodiments;
(iii) a binder, selected from hydroxypropyl methylcellulose, povidone or hydroxypropyl cellulose, in an amount of 4% to 10% by weight; selected from hydroxypropyl methylcellulose in some embodiments, in an amount of 4% to 7% in some embodiments, or in an amount of 5% to 7% in some embodiments, or in an amount of 5% in some embodiments, or in an amount of 6% in some embodiments, or in an amount of 7% in some embodiments;
(iv) a disintegrating agent selected from croscarmellose sodium, croscarmellose calcium, crospovidone or carboxymethyl starch sodium, in an amount of 2% to 10% by weight; selected from croscarmellose sodium in some embodiments, the amount being 6% to 10% by weight in some embodiments, or in an amount of 6% to 9% by weight in some embodiments, or in an amount of 6% by weight in some embodiments, or in an amount of 7% by weight in some embodiments, or in an amount of 8% by weight in some embodiments, or in an amount of 9% by weight in some embodiments, or in an amount of 10% by weight in some embodiments;

(v) a lubricating agent selected from magnesium stearate and sodium stearyl fumarate, in an amount of 0.5% to 1% by weight; selected from magnesium stearate in some embodiments, or in an amount of 0.6% to 1% by weight in some embodiments, or in an amount of 0.6% by weight in some embodiments, or in an amount of 0.7% by weight in some embodiments, or in an amount of 0.8% by weight in some embodiments, or in an amount of 0.9% by weight in some embodiments, or in an amount of 1% by weight in some embodiments;

wherein the defined percentage ranges of any individual component may be arbitrarily combined with that of the other component(s), provided the total percentage of the composition is 100%; and wherein the pharmaceutically acceptable salt of the compound of formula (I) has a structure as follows:

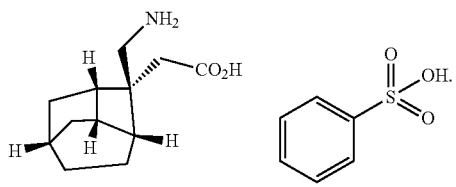

In the composition according to the present disclosure, which is a tablet or capsule formulation, the active material is present, in terms of a free base thereof, in an amount of 1 to 100 mg, or in an amount of 2 to 80 mg in some embodiments, or in an amount of 2 to 60 mg in some embodiments, or in an amount of 2 to 50 mg in some embodiments, or in an amount of 5 to 50 mg in some embodiments, or in an amount of 5 to 40 mg in some embodiments, or in an amount of 5 to 30 mg in some embodiments, or in an amount of 5 to 20 mg in some embodiments, or in an amount of 5 to 10 mg in some embodiments, or in an amount of 10 to 80 mg in some embodiments, or in an amount of 10 to 60 mg in some embodiments, or in an amount of 10 to 50 mg in some embodiments, or in an amount of 20 to 80 mg in some embodiments, or in an amount of 20 to 60 mg in some embodiments, or in an amount of 20 to 50 mg in some embodiments, or in an amount of 30 to 50 mg in some embodiments.

In the composition according to the present disclosure, which is a tablet or capsule formulation, the active material is present, in terms of a free base thereof, in an amount of 5 mg, 10 mg, 15 mg, 20 mg, 25 mg, 30 mg, 35 mg, 40 mg, 45 mg or 50 mg, or in an amount of 5 mg, 10 mg or 20 mg in some embodiments, or in an amount of 5 mg or 20 mg in some embodiments.

According to the present disclosure, there is also provided a method for preparing the pharmaceutical composition, comprising:
(i) subjecting the active materials to a 60-mesh sieve, and subjecting the filler to a 40-mesh sieve for use;
(ii) adding the sieved active substance and filler into a multi-directional movement mixer to be uniformly mixed;
(iii) adding a lubricating agent in the multi-directional movement mixer for mixing with the mixture obtained in (ii);

Or alternatively, when a disintegrating agent or/and a glidant is included in the mixture, adding the lubricating agent, the disintegrating agent and the glidant in the multi-directional movement mixer for mixing with the mixture obtained in (ii); and
(iv) filling a capsule with the mixture obtained in (iii).

According to the present disclosure, there is further provided a method for preparing the pharmaceutical composition, comprising:
(i) subjecting the active materials to a 60-mesh sieve, and subjecting the filler to a 40-mesh sieve for use;
(ii) preparing a 40% aqueous ethanol solution as a solvent;
(iii) adding the sieved active substance and filler with a binder into a wet granulator, and adding the solvent prepared in (ii) for mixing by shearing to prepare a soft material;
(iv) subjecting the soft material to sieving to produce particles, and performing static drying or dynamic drying on fluidized bed;
(v) granulating the dried soft material, and then adding it with a glidant and a disintegrating agent in a multi-directional movement mixer for uniform mixing;
(vi) adding a lubricating agent in the multi-directional movement mixer for mixing; and
(vii) filling a capsule with the mixture obtained in (vi).

Or alternatively, the steps (ii) and (iii) may be replaced by:
(ii-1) formulating a binder and a 40% aqueous ethanol solution into a binder solution;
(iii-1) adding the active material and filler into a wet granulator, and adding the binder solution prepared in (ii-1) for mixing by shearing to prepare a soft material.

According to the present disclosure, there is further provided a method for preparing a pharmaceutical composition in form of tablet, comprising:
(i) subjecting the active materials to a 100-mesh sieve, and subjecting a filler and a disintegrating agent to a 60-mesh sieve;
(ii) adding the sieved active material, filler and disintegrating agent into a high-speed wet granulator for uniform mixing;
(iii) adding a binder solvent into the mixed powder as obtained in (ii) to prepare a soft material;
(iv) subjecting the soft material to a 20-mesh sieve for producing particles, then performing static drying or dynamic drying on fluidized bed to adjust the moisture content to be less than 2%;
(v) subjecting the dried particles to a 24-mesh sieve for granulating, adding the granules with a lubricating agent into a multi-directional movement mixer for uniform mixing;
(vi) press-molding the mixture as obtained in step (v) into tablets.

Or alternatively, the steps (iii) and (iv) may be replaced by:
(iii-1) adding the mixed powder as obtained in step (ii) to a fluidized bed, pumping the binder solution into the fluidized bed with a peristaltic pump, and producing particles by top spray.

The present disclosure also relates to a method for the treating and/or preventing pain, comprising: administering an effective dose of a compound of formula (I) or a pharmaceutically acceptable salt thereof as an active material, wherein the effective dose is 1 to 100 mg in terms of a free salt of the compound of formula (I) or the pharmaceutically acceptable salt thereof, or 5 to 20 mg in certain embodiments, or 5 mg or 20 mg in certain embodiments. The pain includes: postherpetic neuralgia, trigeminal neuralgia, migraine, pain associated with osteoarthritis or joint rheumatism, lower back pain, sciatica, dental pain, pain caused by burns, pain caused by diabetic neuropathy, pain caused by chemotherapy-induced neuropathy, HIV-associated neuralgia, AIDS-associated neuralgia, cancer-associated neuralgia or non-neuropathic pain, acute or chronic tension headache, postoperative pain or fibromyalgia; in certain embodiments, it includes postherpetic neuralgia, pain caused by diabetic neuropathy or fibromyalgia.

The administration route in the treatment method according to the present disclosure is oral administration.

The present disclosure also relates to the use of the pharmaceutical composition in the preparation of a medication for treating and/or preventing pain. The pain includes: postherpetic neuralgia, trigeminal neuralgia, migraine, pain associated with osteoarthritis or joint rheumatism, lower back pain, sciatica, dental pain, pain caused by burns, pain caused by diabetic neuropathy, pain caused by chemotherapy-induced neuropathy, HIV-associated neuralgia, AIDS-associated neuralgia, cancer-associated neuralgia or non-neuropathic pain, acute or chronic tension headache, postoperative pain or fibromyalgia; in certain embodiments, it includes postherpetic neuralgia, pain caused by diabetic neuropathy or fibromyalgia.

Unless stated to the contrary, the terms used in the specification and claims have the following meanings.

The term "an effective dose" refers to an amount of a compound that causes physiological or medical response as required in a tissue, system, or subject, including an amount of a compound which, when administered to a subject, is sufficient to prevent the occurrence of, or to reduce to some extent, one or more symptoms of a condition or disorder being treated.

In the absence of special instructions, the expression "weight percent" in the present disclosure means the mass percent of a component based on the total mass of the composition, and the weight percent of each component of the formulation, such as a tablet or capsule, refers to the mass percent of such component based on the total components in the formulation, such as a tablet or capsule filler (including active agents and auxiliary materials).

The term "active material" in the present disclosure refers to the compound as represented by formula (I) below:

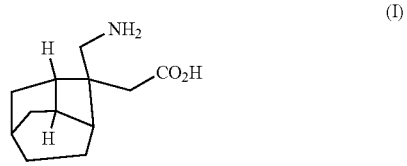 [SMILES: NCC1(CC(=O)O)C2CCC3CC2C1C3]

(I)

or the compound as represented by formula (II) below:

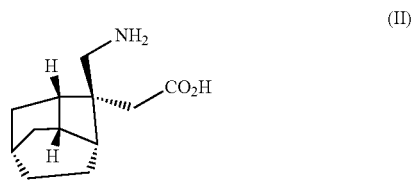 [SMILES: NC[C@@]1(CC(=O)O)[C@@H]2CC[C@H]3C[C@@H]2[C@@H]1C3]

(II)

or a pharmaceutically acceptable salt of the compound of formula (I) or (II), such as:

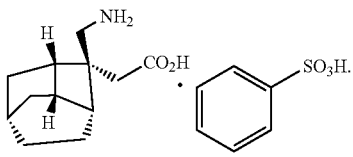

DETAILED DESCRIPTION OF THE DISCLOSURE

Figure 1:
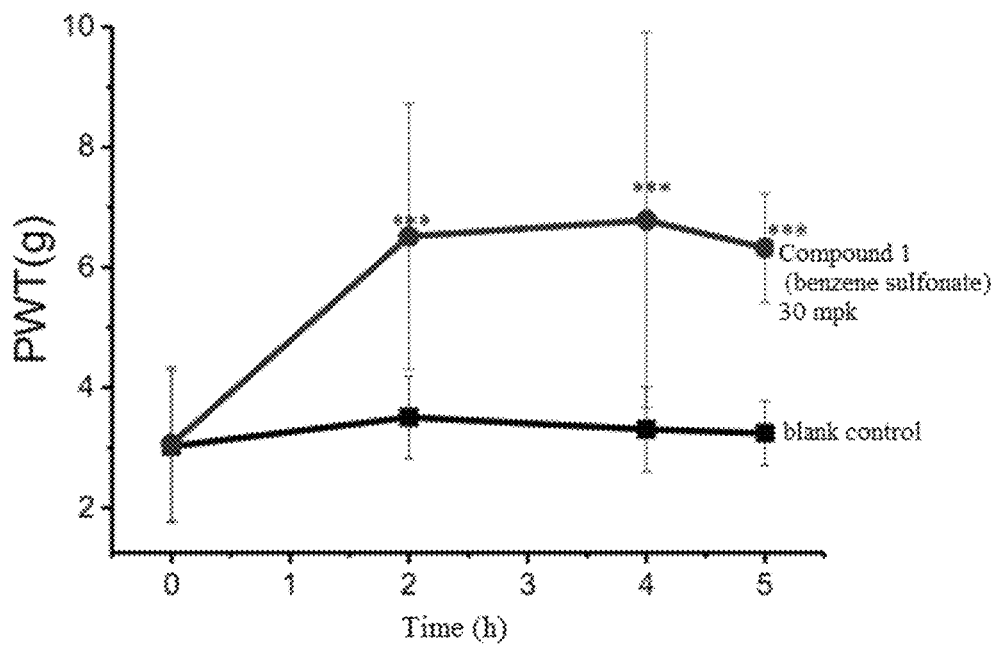
FIG. 1 is a graph showing the effect of the Compound 1 on the mechanical pain threshold value in L5-L6 spinal nerve ligation animal model.

The technical solution of the disclosure is described in detail below in conjunction with drawings and examples in the following, which is, however, merely included in the protection scope of the present disclosure includes without limitation.

The structure of a compound was determined by nuclear magnetic resonance (NMR) and/or mass spectrometry (MS). The NMR shift (δ) was given in $10^{-6}$ ppm. NMR was determined using a nuclear magnetic resonance instrument (Bruker Avance III 400 and Bruker Avance 300) with deuterated dimethyl sulfoxide (DMSO-d6), deuterated chloroform ($CDCl_3$) or deuterated methanol ($CD_3OD$) as a solvent, and tetramethylsilane (TMS) as an internal standard.

The MS measurement was conducted by Agilent 6120 B (ESI) and Agilent 6120 B (APCI).

The HPLC measurement was conducted by Agilent 1260 DAD high-pressure liquid chromatograph (ZorbaxSB-C 18 100×4.6 mm).

The known starting materials in the present disclosure may be synthesized by using or according to methods known in the art, or may be commercially available from companies such as Titan Technologies, Anaji Chemistry, Shanghai Demer, Chengdu Kelong Chemical, Shaoyuan Chemical Technology, Bailingwei Technology, etc.

The microcrystalline cellulose represents microcrystalline cellulose 102, if it is not otherwise specified.

Intermediate 1: The Preparation of Intermediate 1j

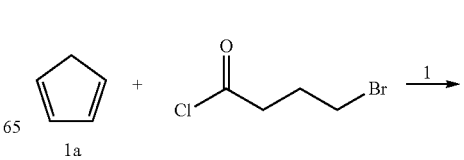

1a

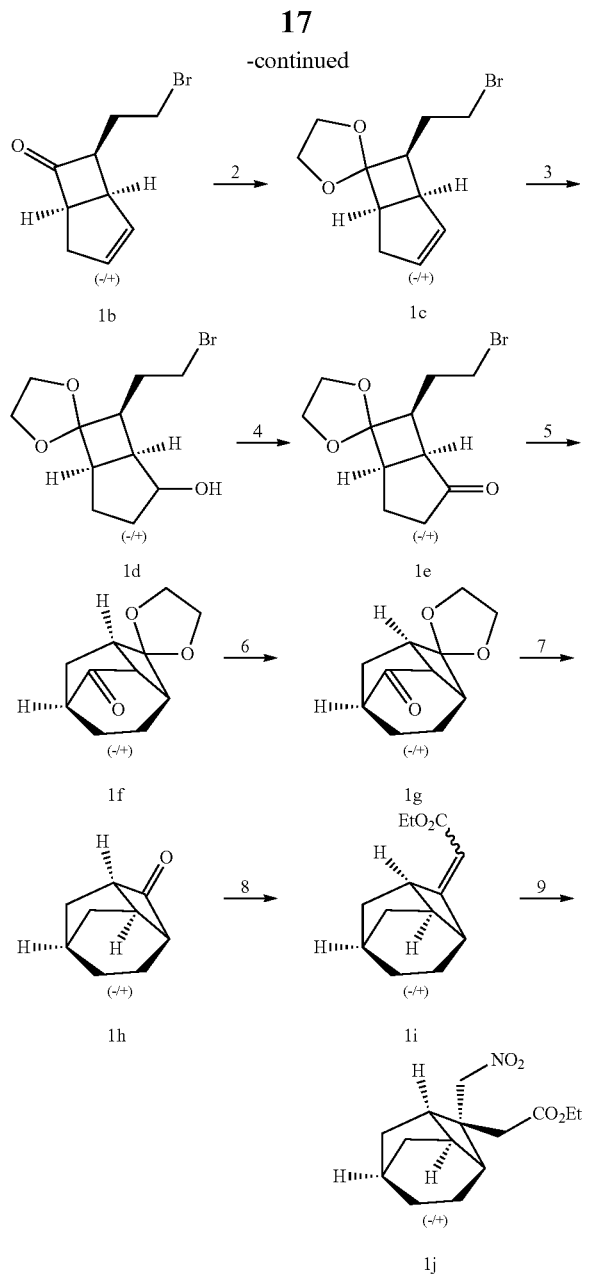

Step 1: (±) (1S, 5R, 7S)-7-(2-bromoethyl)bicyclic [3.2.0]hept-2-ene-6-one (1b)

thereinto, and heated to reflux. A solution of 4-bromobutanoyl chloride (46 g, 0.25 mol) in cyclohexane was added dropwise with a syringe pump (100 mL, 25 ml/h), thereafter a reflux reaction was carried out for 4 hours. The reaction solution was suction filtered, washed with cyclohexane (150 mL×3), and the filtrates were combined, washed with saturated ammonium chloride (1000 mL×2) and water (1000 mL×2), dried over anhydrous sodium sulfate, filtered, concentrated under reduced pressure, and purified by silica gel column chromatography (petroleum ether/ethyl acetate (v/v)= 80:1) to give a light yellow oily product 1b (9.6 g, yield 18%). $^1$H NMR (400 MHz, CDCl$_3$) δ 5.97-5.85 (m, 1H), 5.80-5.70 (m, 1H), 3.91-3.79 (m, 1H), 3.67 (dd, J=9.7, 5.5 Hz, 2H), 3.47 (t, J=6.8 Hz, 2H), 2.68 (ddd, J=18.3, 15.2, 3.9 Hz, 1H), 2.47-2.31 (m, 1H), 2.13 (dq, J=21.0, 6.5 Hz, 1H), 1.93 (ddd, J=21.5, 12.2, 7.1 Hz, 1H)

Step 2: (±) (1S, 5R, 7S)-7-(2-bromoethyl) spiro [bicyclic[3.2.0]hept-[2]-ene-6, 2'-[1,3]dioxolane](1c)

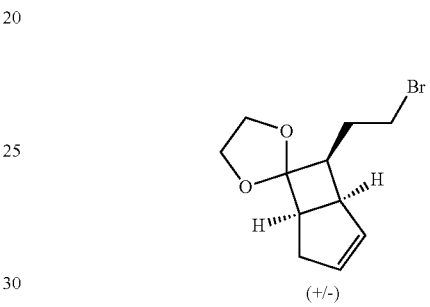

The compound 1b (23 g, 0.11 mol), p-toluenesulfonic acid monohydrate (1.0 g, 5.5 mmol), and ethylene glycol (27.3 g, 0.44 mol) were taken into a single-necked flask, added with 250 mL of toluene, and heated for refluxing and water separation for 6 h. Upon cooling, the reaction solution was poured into ice water, added with sodium bicarbonate to adjust the pH value to neutral, and extracted with ethyl acetate (300 mL×3). The organic phases were combined, dried with anhydrous sodium sulfate, filtered, concentrated, and purified by column chromatography (ethyl acetate: petroleum ether=1:30) to obtain a yellow oily product 1c (21.2 g, yield 75%). $^1$H NMR (400 MHz, CDCl$_3$) δ 5.94-5.83 (m, 1H), 5.67-5.56 (m, 1H), 3.95-3.75 (m, 4H), 3.36-3.25 (m, 2H), 3.23-3.12 (m, 1H), 3.02 (ddd, J=22.9, 15.7, 8.0 Hz, 2H), 2.48-2.25 (m, 2H), 1.99-1.78 (m, 2H).

Step 3: (±) (1S, 5R, 7S)-7-(2-bromoethyl) spiro [bicyclic[3.2.0]hept-[2]-ene-6,2'-[1,3]dioxolane]-2-ol (1d)

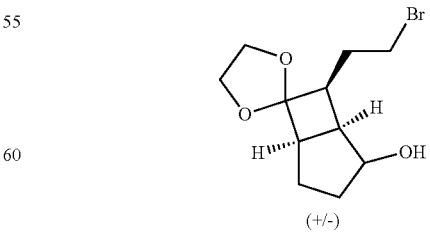

A starting material 1a (24 g, 0.36 mol) and 1100 mL of cyclohexane were added into a reaction flask protected with nitrogen, and triethylamine (25 g, 0.25 mol) was added The starting material 1c (15 g, 0.06 mol) was added into a reaction flask, added with tetrahydrofuran (250 ml) as a solvent, and added dropwise with a borane dimethyl sulfide solution (30 ml, 0.3 mol) in an ice-water bath. Then, the resultant was left stand at the temperature for 2 hours, added dropwise with a purified water (0.6 mol) in the ice-water bath, then added dropwise with a sodium hydroxide aqueous solution (3 mol/1,200 ml), then added dropwise with hydrogen peroxide (containing 0.6 mol of $H_2O_2$). Then it is heated to room temperature to react for 3 hours. Thereafter, it is extracted with ethyl acetate (200 mL×3), and the organic phases were combined, washed with water (300 mL×2), dried over anhydrous sodium sulfate, filtered and concentrated under reduced pressure to give a pale yellow oily product 1d (16.5 g), which was used in the next step without purification.

Step 4: (±) (1S, 5R, 7S)-7-(2-bromoethyl) spiro[bicyclic[3.2.0]hept-[2]-ene-6,2'-[1,3]dioxolane]-2-one (1e)

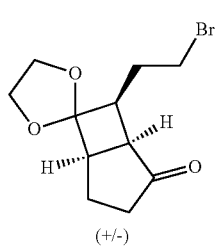 [SMILES: O=C1CC[C@@H]2[C@H]1[C@H](CCBr)C21OCCO1]

(+/-)

The compound 1d (16.5 g, 0.06 mol) and dichloromethane (250 mL) were added to a reaction flask, and added with a Dess-Martin oxidant (38.2 g, 0.09 mol) in batch manner in an ice bath, and reacted at room temperature for 2 hours. A saturated sodium bicarbonate solution was added dropwise to the reaction solution until the pH was about 7. The resultant was subjected for liquid separation, and the aqueous phase was extracted with dichloromethane (200 mL×2), while the organic phases were combined, washed with water (500 mL×1), dried over anhydrous sodium sulfate, filtered, concentrated under reduced pressure, and purified by silica gel column chromatography (petroleum ether/ethyl acetate (v/v)=8:1) to give a light yellow oily product 1e (9.7 g, yield 59%). $^1$H NMR (400 MHz, CDCl$_3$) δ 4.02-3.81 (m, 4H), 3.40 (dd, J=10.3, 3.8 Hz, 2H), 3.15 (td, J=10.3, 4.9 Hz, 2H), 2.61 (ddd, J=20.6, 14.0, 8.1 Hz, 2H), 2.27 (ddt, J=18.9, 9.6, 1.8 Hz, 1H), 2.12-2.00 (m, 1H), 1.99-1.70 (m, 3H).

Step 5: (±) (1'R, 3'S, 6'S)-spiro[[1,3]dioxolane-2,2'-tricyclic[4.2.1.0$^{3,8}$]nonane]-7'-one (1f)

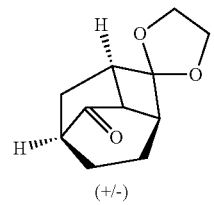 [SMILES: O=C1C2[C@H]3C[C@@H]1CC[C@@H]2C31OCCO1]

(+/-)

Potassium tert-butoxide (16 g, 0.14 mol) and tetrahydrofuran (1L) were added to a reaction flask under protection of nitrogen. The resultant was cooled to −0° C., added dropwise with the compound 1e in toluene (29 g, 0.11 mol), and then stirred at room temperature for 2 hours. A saturated ammonium chloride solution was added dropwise in an ice bath until the pH was about 7, extracted with ethyl acetate (500 mL×2), washed with water (1000 mL×2), dried over anhydrous sodium sulfate, filtered, concentrated under reduced pressure, and purified by silica gel column chromatography (petroleum ether/ethyl acetate (v/v)=10:1) to give a pale yellow oily product 1f (9.5 g, yield 45%). $^1$H NMR (400 MHz, CDCl$_3$) δ 4.04-3.86 (m, 4H), 3.20-3.07 (m, 1H), 2.99-2.86 (m, 1H), 2.53 (ddd, J=8.6, 5.6, 1.7 Hz, 1H), 2.41-2.24 (m, 2H), 2.24-2.01 (m, 2H), 1.95 (d, J=13.2 Hz, 1H), 1.61 (dddd, J=14.4, 7.6, 2.6, 0.7 Hz, 1H), 1.51-1.38 (m, 1H).

Step 6: (±) (1'R, 3'S, 6'S)-spiro[[1,3]dioxolane-2,2'-tricyclic[4.2.1.0$^{3,8}$]nonane](1g)

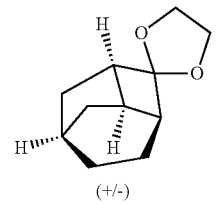 [SMILES: C1COC2(O1)[C@@H]1C[C@@H]3CC[C@H]2[C@H]1C3]

(+/-)

The starting material 1f (9.0 g, 46.3 mmol) and diethylene glycol (150 mL) were added into a reaction flask, added with hydrazine hydrate (8.9 g, 278 mmol) and potassium hydroxide (15.6 g, 278 mmol). The resultant was reacted at 180° C. for 3 hours, followed by a rotary evaporation under reduced pressure for water removal at 70° C., then warmed to 220° C. and reacted for 2 hours, and cooled. The resulting reaction solution was added with water (200 mL), extracted with methyl tert-butyl ether (300 mL×3), washed with 1 mol/l hydrochloric acid (400 mL×2), washed with water (400 mL×2), dried with anhydrous sodium sulfate, filtered, concentrated under reduced pressure and purified by silica gel column chromatography (petroleum ether/ethyl acetate (v/v)= 60:1) to give a colorless oily product 1g (3 g), which was used in the next step without purification.

Step 7: (±) (1R, 3S, 6R, 8R)-tricyclic[4.2.1.0$^{3,8}$]nonane-2-one (1h)

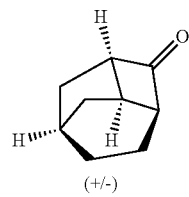

(+/-)

The starting material 1g (3 g, 16.6 mmol) was added to a reaction flask, then added with tetrahydrofuran (36 ml) and water (12 ml) as solvents, and added dropwise with trifluoroacetic acid (8 ml) in an ice bath, and reacted at 45° C. for 3 hours. The resultant was added dropwise with a saturated sodium bicarbonate solution in an ice bath until the pH was about 7, then extracted with ethyl acetate (80 mL×3), washed with water (100 mL×2), dried over anhydrous sodium sulfate, filtered, concentrated under reduced pressure, and purified by silica gel column chromatography (petroleum ether/ethyl acetate (v/v)=100:1) to give a white solid product 1h (2 g, yield 88%). ¹H NMR (400 MHz, CDCl₃) δ 3.47-3.33 (m, 1H), 3.19 (dd, J=3.3, 1.8 Hz, 1H), 2.84-2.69 (m, 1H), 2.47-2.32 (m, 1H), 2.12-1.97 (m, 1H), 1.93 (d, J=12.3 Hz, 1H), 1.82-1.69 (m, 1H), 1.56-1.35 (m, 4H), 1.27-1.10 (m, 1H).

Step 8: (±) ethyl 2-((1R, 3S, 6R, 8R)-tricyclic [4.2.1.0³,⁸]non-2-ylidene) acetate (1i)

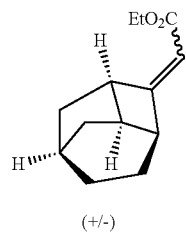

(+/-)

Sodium hydride (60%, 91.6 g, 3.82 mol) and tetrahydrofuran (5L) were added to a reaction flask, cooled to 0° C., and added dropwise with ethyl diethoxyphosphono ethylacetate (856 g, 3.82 mol) in tetrahydrofuran (400 mL). Then, the resultant was left stand at the temperature for 15 minutes, and added dropwise with the compound 1h (400 g, 2.94 mol) in tetrahydrofuran (200 mL), and then heated to room temperature for reaction for 1 hour. The resultant was added with a saturated ammonium chloride dropwise to pH 7-8 in an ice water bath, extracted with ethyl acetate (500 mL×3), washed with saturated brine (500 mL×2), dried over anhydrous sodium sulfate, concentrated under reduced pressure, and purified by silica gel column chromatography (petroleum ether/ethyl acetate (v/v)=30:1) to give a light yellow oily product 1i (310 g, 51% yield).

Step 9: (±) ethyl 2-((1R, 3S, 6R, 8R)-2-(nitromethyl) tricyclic[4.2.1.0³,⁸]non-2-yl) acetate (1j)

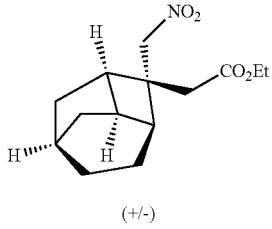 [SMILES: CCOC(=O)C[C@]1(C[N+](=O)[O-])[C@@H]2C[C@@H]3CC[C@H]1[C@H]2C3]

(+/-)

The starting material 1i (390 g, 1.89 mol), nitromethane (4L) and 1,8-diazabicyclo[5.4.0]undec-7-ene (575.6 g, 3.78 mol) were added to a reaction flask and was heated to 80° C. for 9 hours. The reaction liquid was poured into ice water (3000 ml), extracted with DCM (2000 mL×3), washed with brine (3000 ml), dried over anhydrous sodium sulfate, concentrated under reduced pressure, and purified by silica gel column chromatography (petroleum ether/ethyl acetate (v/v)=100:1) to give a colorless oily product 1j (360 g, yield 71%).

The Preparation of Compound 1:

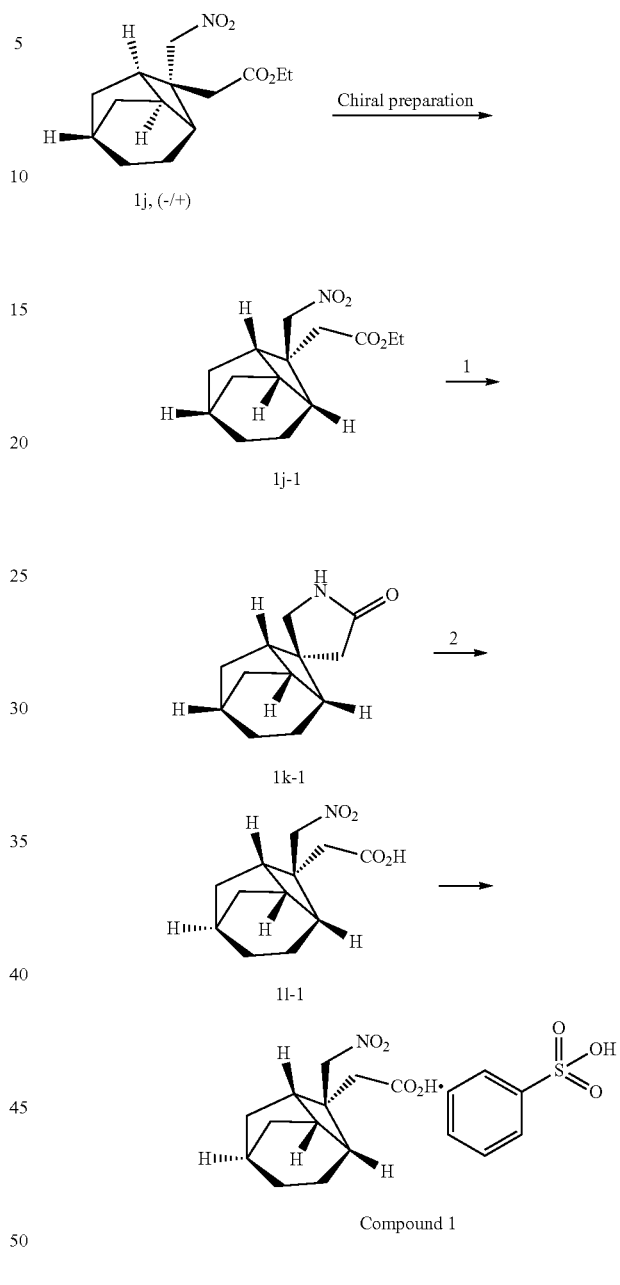

(±) ethyl 2-((1R, 3S, 6R, 8R)-2-(nitromethyl) tricyclic [4.2.1.0³,⁸]non-2-yl)acetate (intermediate 1j) (360 g) was used for resolution under the following condition: using Thar analytical SFC (SFC-A) as an instrument, chiralPak AD, 150×4.6 mm I.D. 3 us m as a column, with mobile phases of A for CO₂ and B for Methanol, gradient of B as 5-40%, a flow velocity of 2.4 mL/min, and a column temperature of 35° C. Two optical isomers were obtained after separation: peak 1 (retention time: 3.8 minutes, 174 g) and peak 2 (retention time: 5.7 minutes, 160 g). Compound 1j: [α] 20D=0.00° (C=0.9, CH2Cl2); peak 2: [α] 20D=440 (C=0.103, CH3OH). Here, C refers to the weight (in g) of the substance to be tested per 100 mL of solution, and 20D refers to a test at 20° C., with a sodium light lamp as a light source, at a wavelength of 589 nm.

Step 1: (1'S, 2'S, 3'R, 6'S, 8'S)-spiro[pyrrolidine-3,2'-tricyclic[4.2.1.0³,⁸]nonane]-5-one (1k-1)

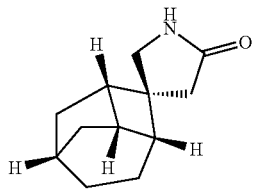

The starting material 1j-1 (peak 2, 270 g, 1.01 mol), ethanol (1L) and water (1L) were added to a reaction flask, then added with reduced iron powders (282 g, 5.05 mol) and ammonium chloride (162 g, 3.03 mol), and reacted under refluxing for 4 hours. The reaction solution was filtered, and the filtrate was concentrated to remove ethanol, thereafter the remaining solution was added with 500 mL of water, while the filter residue was washed with dichloromethane (200 mL×3). The filtrate was collected, and the organic phase was mixed with the aforesaid remaining solution, subjected to liquid separation, extracted with dichloromethane twice (500 mL×2). The organic phases were combined, washed with water (500 mL×2), dried with sodium sulfate, concentrated under reduced pressure, and purified by silica gel column chromatography (dichloromethane/methanol (v/v)=40: 1-10:1) to obtain a white solid product 1k-1 (160 g, yield 83%).

Step 2: 2-((1S, 2S, 3R, 6S, 8S)-2-(aminomethyl)tricyclic[4.2.1.0³¹,]non-2-yl) acetic acid (11-1)

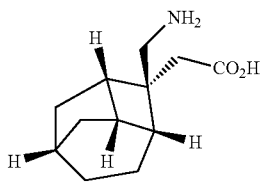

The starting material 1k-1 (320 g, 1.673 mol) was added to a reaction flask, then added with 6N hydrochloric acid (1.6 L), and reacted under refluxing for 16 h. The precipitated solid was filtered. The obtained solid was dissolved in 1L of purified water, adjusted with concentrated ammonia water until the pH was about 7, subjected to suction filtration, washed with ice water, and dried to obtain a white solid. The filtrate was adjusted with 10N sodium hydroxide in an ice water bath until the pH was about 6, and further adjusted with concentrated ammonia water until the pH was about 7, and extracted with dichloromethane (1L×3). The remaining aqueous phase was concentrated and dried, filtered, and washed with ice water to obtain a white solid. The resulting solid as obtained in the two portions was pulped with dichloromethane (1.5 L×3) to give a white solid compound 11-1 (245 g, 70%).

The Preparation of Compound 1:

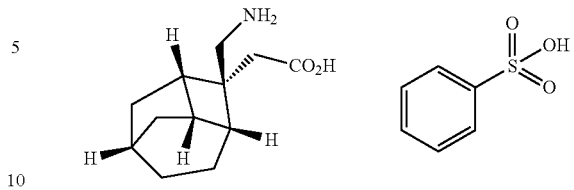

The compound 11-1 (245 g, 1.17 mol) was added into a reaction flask, added with methanol (2.2L), and added dropwise with benzenesulfonic acid monohydrate (268.0 g, 1.52 mol) in methanol, then stirred for 1 hour at room temperature. The precipitated solid was filtered by suction, and the filtrate was concentrated to obtain a solid. The resulting solid in the two portions was combined and pulped with dichloromethane (1.5 L×3), filtered, washed with ethyl acetate, and dried to obtain a pure compound 1 (398 g, yield 92.5%, HPLC: 99%, with a chemical formula of $C_{12}H_{19}NO_2 \cdot C_6H_6O_3S$). $^1H$ NMR (400 MHz, $D_2O$) δ 7.85-7.70 (m, 2H), 7.54 (tt, J=14.3, 7.2 Hz, 3H), 3.33 (d, J=13.8 Hz, 2H), 2.81 (dd, J=13.2, 5.4 Hz, 1H), 2.57 (q, J=17.6 Hz, 2H), 2.47-2.37 (m, 1H), 2.27 (dd, J=12.0, 6.0 Hz, 1H), 2.17-2.06 (m, 1H), 1.96 (dd, J=21.6, 9.5 Hz, 1H), 1.79-1.66 (m, 1H), 1.66-1.40 (m, 4H), 1.33 (dd, J=14.3, 9.0 Hz, 1H), 1.26-1.15 (m, 1H).

Figure 4:
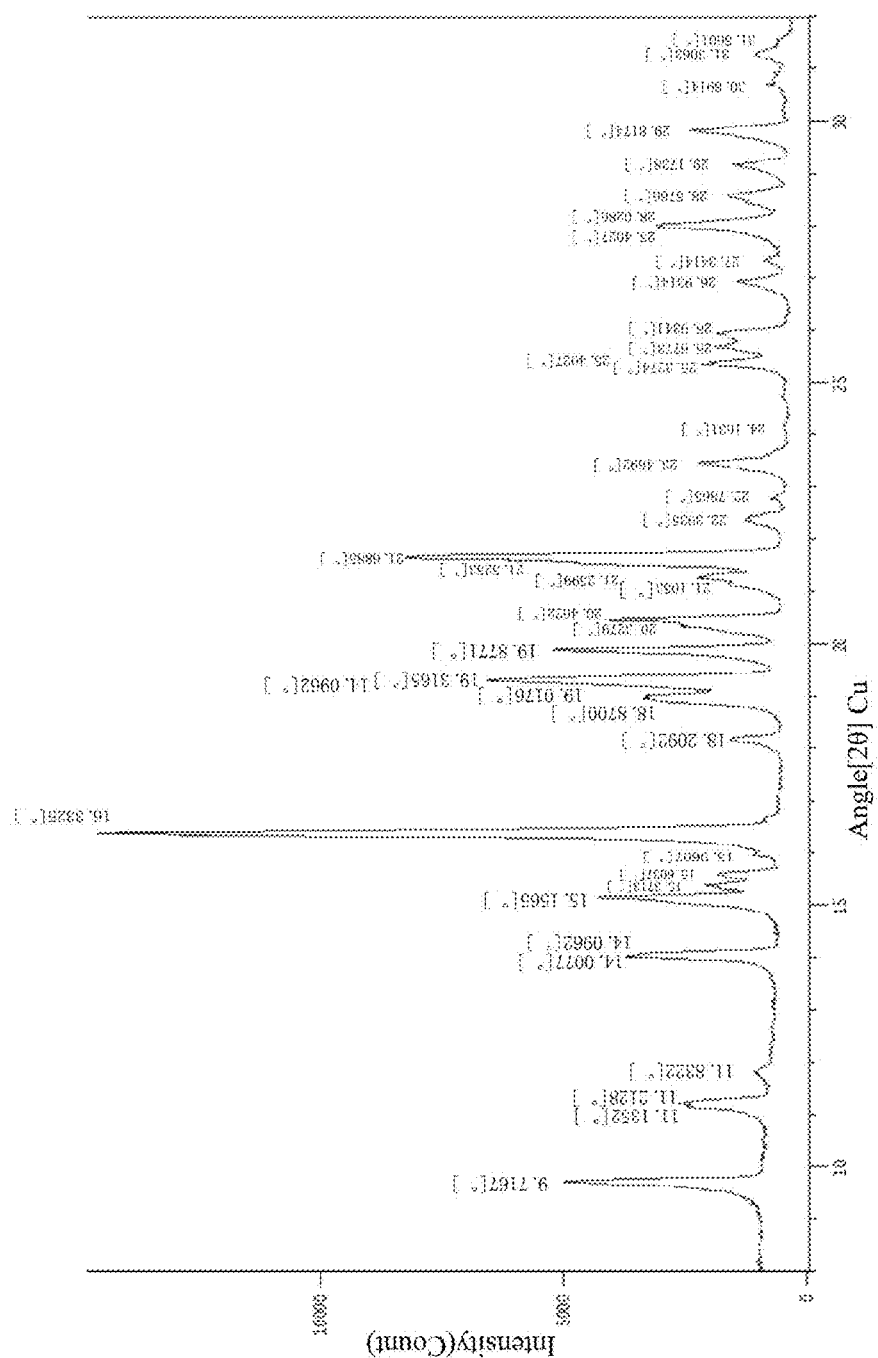
FIG. 4 is graph showing the XRD of Compound 1.

The peak value of compound 1 in the X-ray powder-diffraction pattern (XRD) is shown in the table as below, and specifically shown in FIG. 4.

| 2θ | Peak height | FWHM | Interplanar spacing [Å] | Relative peak height [%] |
| --- | --- | --- | --- | --- |
| 9.7167 | 4046.64 | 0.1279 | 9.10278 | 33.05 |
| 11.1352 | 1612.11 | 0.0384 | 7.94615 | 13.17 |
| 11.2128 | 1820.68 | 0.1023 | 7.89135 | 14.87 |
| 11.8322 | 277.75 | 0.1535 | 7.47961 | 2.27 |
| 14.0077 | 3132.13 | 0.0512 | 6.32246 | 25.58 |
| 14.0962 | 2255.84 | 0.064 | 6.28296 | 18.43 |
| 15.1565 | 3670.71 | 0.064 | 5.84573 | 29.98 |
| 15.3713 | 1403.94 | 0.0768 | 5.76452 | 11.47 |
| 15.6037 | 1165.35 | 0.1279 | 5.67918 | 9.52 |
| 15.9607 | 443.05 | 0.0512 | 5.55295 | 3.62 |
| 16.3325 | 12242.87 | 0.1023 | 5.42737 | 100 |
| 18.2092 | 900.66 | 0.1151 | 4.87203 | 7.36 |
| 18.87 | 1903.14 | 0.064 | 4.70287 | 15.54 |
| 19.0176 | 2554.83 | 0.0384 | 4.66672 | 20.87 |
| 19.3165 | 5667.72 | 0.1279 | 4.59518 | 46.29 |
| 19.8771 | 4571.39 | 0.0895 | 4.46681 | 37.34 |
| 20.3279 | 1930.15 | 0.0384 | 4.36878 | 15.77 |
| 20.4622 | 3513.85 | 0.0768 | 4.3404 | 28.7 |
| 21.1053 | 859.6 | 0.0768 | 4.20958 | 7.02 |
| 21.2599 | 1641.19 | 0.0512 | 4.17932 | 13.41 |
| 21.5253 | 3785.86 | 0.0384 | 4.12837 | 30.92 |
| 21.6885 | 7208.47 | 0.1151 | 4.09769 | 58.88 |
| 22.3935 | 724.03 | 0.1535 | 3.97025 | 5.91 |
| 22.7865 | 262.87 | 0.0384 | 3.90265 | 2.15 |
| 23.4692 | 1810.44 | 0.0895 | 3.79065 | 14.79 |
| 24.1631 | 54.8 | 0.1535 | 3.68334 | 0.45 |
| 25.3274 | 1659.16 | 0.0624 | 3.51369 | 13.55 |
| 25.4027 | 1478.13 | 0.0512 | 3.50635 | 12.07 |
| 25.6773 | 1433.37 | 0.0512 | 3.46946 | 11.71 |
| 25.9344 | 1421.23 | 0.0468 | 3.4328 | 11.61 |
| 25.999 | 1046.47 | 0.0468 | 3.43294 | 8.55 |
| 26.9314 | 950.92 | 0.1404 | 3.30794 | 7.77 |
| 27.3414 | 296.52 | 0.1248 | 3.25927 | 2.42 |
| 27.9554 | 2439.22 | 0.0468 | 3.18906 | 19.92 |
| 28.0286 | 2418.82 | 0.0624 | 3.1809 | 19.76 |
| 28.5766 | 1038.14 | 0.078 | 3.12113 | 8.48 |
| 29.1738 | 996.82 | 0.0468 | 3.05858 | 8.14 |
| 29.8174 | 1938.81 | 0.1248 | 2.99402 | 15.84 |
| 30.6914 | 348.82 | 0.0468 | 2.91071 | 2.85 |
| 31.3063 | 653.82 | 0.1248 | 2.85493 | 5.34 |

-continued

| 2θ | Peak height | FWHM | Interplanar spacing [Å] | Relative peak height [%] |
|---|---|---|---|---|
| 31.5601 | 212.27 | 0.0936 | 2.83255 | 1.73 |
| 32.3291 | 96.39 | 0.1872 | 2.76691 | 0.79 |
| 33.0473 | 214.64 | 0.1872 | 2.7084 | 1.75 |
| 34.2421 | 109.66 | 0.1248 | 2.61658 | 0.9 |
| 35.264 | 437.3 | 0.078 | 2.54306 | 3.57 |
| 35.5326 | 412.09 | 0.0468 | 2.52445 | 3.37 |
| 36.1622 | 418.43 | 0.156 | 2.48193 | 3.42 |
| 36.6015 | 376.67 | 0.1872 | 2.45315 | 3.08 |
| 37.239 | 295.68 | 0.156 | 2.4126 | 2.42 |
| 37.714 | 195.04 | 0.1092 | 2.3833 | 1.59 |
| 35.5326 | 412.09 | 0.0468 | 2.52445 | 3.37 |

Figure 5:
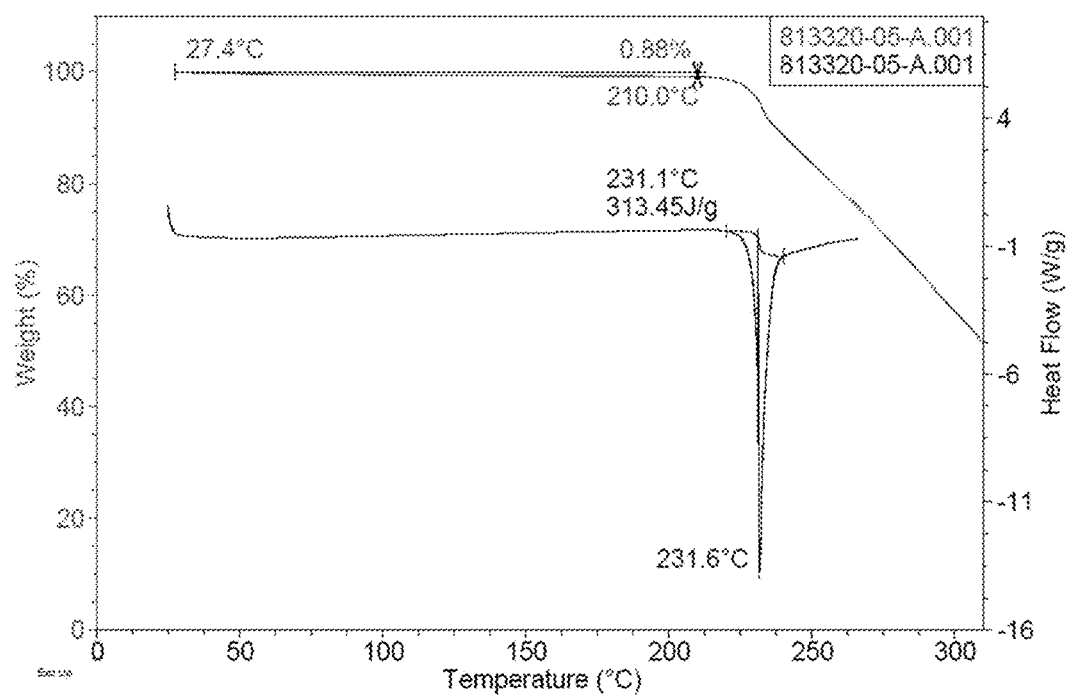
FIG. 5 is graph showing the TGA/DSC of Compound 1.
Figure 6:
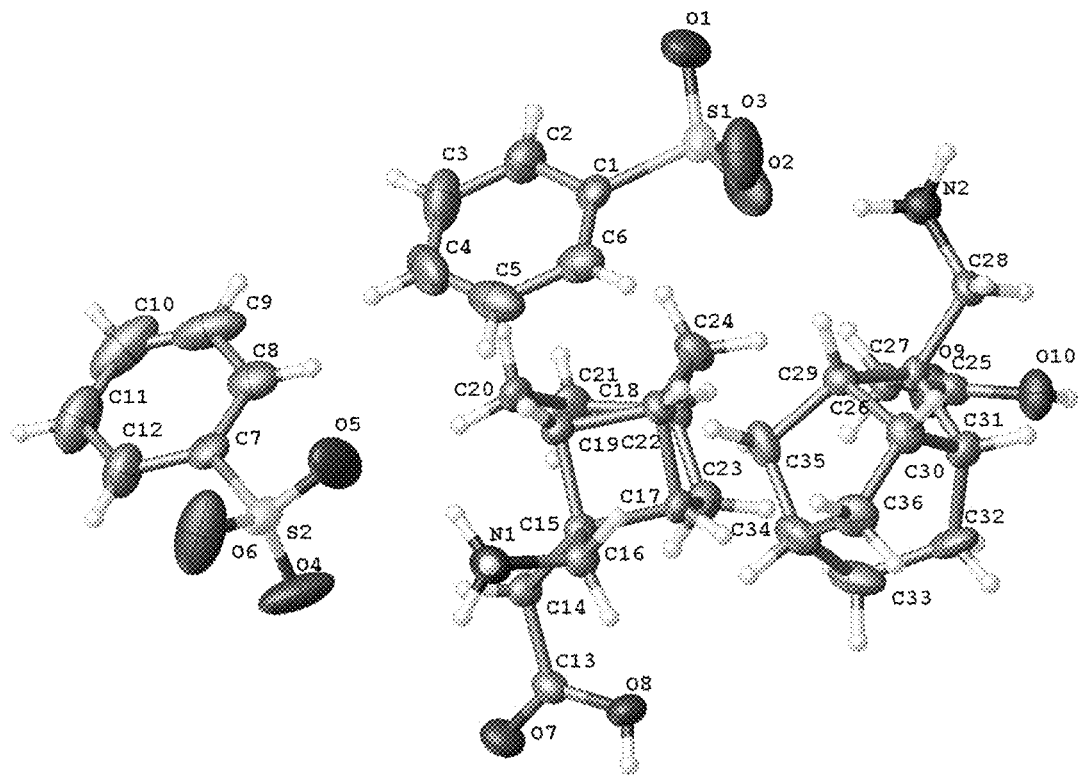
FIG. 6 is a diagram depicting the single-crystal diffraction spectrum of Compound 1.

The spectra of TGA/DSC of Compound 1 is shown in FIG. 5, and the single-crystal diffraction spectrum thereof is shown in FIG. 6.

Example 1: Compatibility of Auxiliary Material and Compound 1

The mixture of active material compound 1 and various types of filler was prepared according to table 1, and placed uncovered under a condition of a moisture and heat of 75% RH and 40° C., then was measured for its impurity content, respectively. The testing results for impurity are shown in Table 2.

TABLE 1

Mixtures of Compound 1 with various types of fillers

| Materials | Scheme 1 | Scheme 2 | Scheme 3 | Scheme 4 | Scheme 5 | Scheme 6 | Scheme 7 | Scheme 8 |
|---|---|---|---|---|---|---|---|---|
| Compound 1 | 1 part | 1 part | 1 part | 1 part | 1 part | 1 part | 1 part | 1 part |
| Mannitol | 5 parts | 0 | 0 | 0 | 0 | 0 | 0 | 0 |
| Lactose | 0 | 5 parts | 0 | 0 | 0 | 0 | 0 | 0 |
| Starch | 0 | 0 | 5 parts | 0 | 0 | 0 | 0 | 0 |
| Pregelatinized starch | 0 | 0 | 0 | 5 parts | 0 | 0 | 0 | 0 |
| Sorbitol | 0 | 0 | 0 | 0 | 5 parts | 0 | 0 | 0 |
| Saccharose | 0 | 0 | 0 | 0 | 0 | 5 parts | 0 | 0 |
| Low-substituted hydroxypropyl cellulose | 0 | 0 | 0 | 0 | 0 | 0 | 5 parts | 0 |
| Microcrystalline cellulose | 0 | 0 | 0 | 0 | 0 | 0 | 0 | 5 parts |

The preparation of the mixture of Compound 1 and various types of fillers was as follows:
(1) subjecting Compound 1 to a 60-mesh sieve, and subjecting the filler to a 40-mesh sieve for use;
(2) mixing Compound 1 and the filler uniformly to obtain a mixed powder;
(3) placing a sample uncovered under a condition of a moisture and heat of 75% RH and 40° C..

TABLE 2 the variations in the impurity content in the mixture of Compound 1 and various fillers

| | Total impurity/% | | | |
|---|---|---|---|---|
| No. | Day 0 | Day 7 | Day 14 | Day 30 |
| Scheme 1 | 0.054 | 0.056 | 0.064 | 0.173 |
| Scheme 2 | 0.061 | 0.068 | 0.166 | 0.297 |
| Scheme 3 | 0.054 | 0.068 | 0.123 | 0.282 |
| Scheme 4 | 0.059 | 0.139 | 0.272 | 0.381 |
| Scheme 5 | 0.064 | 0.078 | 0.148 | 0.298 |
| Scheme 6 | 0.062 | 0.185 | 0.312 | 0.425 |
| Scheme 7 | 0.068 | 0.098 | 0.112 | 0.188 |
| Scheme 8 | 0.042 | 0.056 | 0.057 | 0.063 |

Conclusion: the mannitol, low-substituted hydroxypropyl cellulose and microcrystalline cellulose have good compatibility with Compound 1.

Example 2: The Effect of Various Types of Fillers on the Mixing Uniformity of the Capsule Formulation The capsules of Compound 1 are prepared according to Table 3, by a preparation method as follows:
(1) subjecting Compound 1 to a 60-mesh sieve, and subjecting the filler to a 40-mesh sieve for use;
(2) adding the sieved Compound 1 and the filler in a multi-directional movement mixer for uniform mixing;
(3) adding a binder, a disintegrating agent and a glidant into the multi-directional movement mixer for uniform mixing with the mixture in (2);
(4) adding a lubricating agent in the multi-directional movement mixer for a final mixing with the mixture in (3);
(5) selecting an appropriate type of capsule and filling the capsule with the final mixture obtained in (4).

TABLE 3 the capsules with various fillers formulation

| No. | Raw materials | Amount | composition of a single dosage, by weight percent | Functions |
| --- | --- | --- | --- | --- |
| Formulation 1 | Compound 1 (in terms of $C_{12}H_{19}NO_2 \cdot C_6H_6O_3S$) | 1 part | 4.08 | Active material |
| | Mannitol | 20 parts | 81.63 | Filler |
| | Hydroxypropyl Cellulose | 1 part | 4.08 | Binder |
| | Silica | 1 part | 4.08 | Glidant |
| | Croscarmellose sodium | 1 part | 4.08 | Disintegrating agent |
| | Magnesium stearate | 0.5 part | 2.04 | Lubricating agent |
| | Gelatin capsule | 1 capsule | 1 capsule | — |
| Formulation 2 | Compound 1 (in terms of $C_{12}H_{19}NO_2 \cdot C_6H_6O_3S$) | 1 part | 4.08 | Active material |
| | Low-substituted hydroxypropyl cellulose | 20 parts | 81.63 | Filler |
| | Hydroxypropyl Cellulose | 1 part | 4.08 | Binder |
| | Silica | 1 part | 4.08 | Glidant |
| | Croscarmellose sodium | 1 part | 4.08 | Disintegrating agent |
| | Magnesium stearate | 0.5 part | 2.04 | Lubricating agent |
| | Gelatin capsule | 1 capsule | 1 capsule | — |
| Formulation 3 | Compound 1 (in terms of $C_{12}H_{19}NO_2 \cdot C_6H_6O_3S$) | 1 part | 4.08 | Active material |
| | Microcrystalline cellulose 12 | 20 parts | 81.63 | Filler |
| | Hydroxypropyl Cellulose | 1 part | 4.08 | Binder |
| | Silica | 1 part | 4.08 | Glidant |
| | Croscarmellose sodium | 1 part | 4.08 | Disintegrating agent |
| | Magnesium stearate | 0.5 part | 2.04 | Lubricating agent |
| | Gelatin capsule | 1 capsule | 1 capsule | — |

The capsules of Compound 1 were assayed by high-performance liquid chromatography, according to General Rule 0941 "a test method for content uniformity" in Chinese Pharmacopoeia, 2015 edition. The results are shown in Table 4.

TABLE 4

Uniformity of the capsules of Compound 1

| No. | Value of A + 2.2S | RSD % |
|---|---|---|
| Formulation 1 | 10.75 | 6.56 |
| Formulation 2 | 12.64 | 7.42 |
| Formulation 3 | 8.42 | 4.38 |

Example 3: The Effect of the Combination of Various Types of Fillers on Formulation Stability and Content Uniformity The capsules of Compound 1 were prepared according to the ratios in Table 5, by the preparation method as shown in Example 2, and the content uniformity and stability thereof were measured.

TABLE 5

The raw materials for the capsules of Compound 1

| No. | Raw materials | Amount | The composition of a single dosage, by weight percent | Functions |
|---|---|---|---|---|
| Formulation 4 | Compound 1 (in terms of $C_{12}H_{19}NO_2 \cdot C_6H_6O_3S$) | 1 part | 3.92 | Active material |
|  | Mannitol | 7 parts | 27.45 | Filler |
|  | Low-substituted hydroxypropyl cellulose | 7 parts | 27.45 | Filler |
|  | Microcrystalline cellulose 102 | 7 parts | 27.45 | Filler |
|  | Hydroxypropyl Cellulose | 1 part | 3.92 | Binder |
|  | Silica | 1 part | 3.92 | Glidant |
|  | Croscarmellose sodium | 1 part | 3.92 | Disintegrating agent |
|  | Magnesium stearate | 0.5 part | 1.96 | Lubricating agent |
|  | Gelatin capsule | 1 capsule | 1 capsule | — |
| Formulation 5 | Compound 1 (in terms of $C_{12}H_{19}NO_2 \cdot C_6H_6O_3S$) | 1 part | 3.92 | Active material |
|  | Mannitol | 0 part | 0.00 | Filler |
|  | Low-substituted hydroxypropyl cellulose | 7 parts | 27.45 | Filler |
|  | Microcrystalline cellulose 102 | 14 parts | 54.90 | Filler |
|  | Hydroxypropyl Cellulose | 1 part | 3.92 | Binder |
|  | Silica | 1 part | 3.92 | Glidant |
|  | Croscarmellose sodium | 1 part | 3.92 | Disintegrating agent |
|  | Magnesium stearate | 0.5 part | 1.96 | Lubricating agent |
|  | Gelatin capsule | 1 capsule | 1 capsule | — |
| Formulation 6 | Compound 1 (in terms of $C_{12}H_{19}NO_2 \cdot C_6H_6O_3S$) | 1 part | 3.92 | Active material |
|  | Mannitol | 7 parts | 27.45 | Filler |
|  | Low-substituted hydroxypropyl cellulose | 0 part | 0.00 | Filler |
|  | Microcrystalline cellulose 102 | 14 parts | 54.90 | Filler |
|  | Hydroxypropyl Cellulose | 1 part | 3.92 | Binder |
|  | Silica | 1 part | 3.92 | Glidant |
|  | Croscarmellose sodium | 1 part | 3.92 | Disintegrating agent |
|  | Magnesium stearate | 0.5 part | 1.96 | Lubricating agent |
|  | Gelatin capsule | 1 capsule | 1 capsule | — |
| Formulation 7 | Compound 1 (in terms of $C_{12}H_{19}NO_2 \cdot C_6H_6O_3S$) | 1 part | 3.92 | Active material |
|  | Mannitol | 7 parts | 27.45 | Filler |
|  | Low-substituted hydroxypropyl cellulose | 14 parts | 54.90 | Filler |
|  | Microcrystalline cellulose 102 | 0 part | 0.00 | Filler |
|  | Hydroxypropyl Cellulose | 1 part | 3.92 | Binder |
|  | Silica | 1 part | 3.92 | Glidant |

TABLE 5-continued

The raw materials for the capsules of Compound 1

| No. | Raw materials | Amount | The composition of a single dosage, by weight percent | Functions |
|---|---|---|---|---|
| | Croscarmellose sodium | 1 part | 3.92 | Disintegrating agent |
| | Magnesium stearate | 0.5 part | 1.96 | Lubricating agent |
| | Gelatin capsule | 1 capsule | 1 capsule | — |
| Formulation 8 | Compound 1 (in terms of $C_{12}H_{19}NO_2 \cdot C_6H_6O_3S$) | 1 part | 9.52 | Active material |
| | Mannitol | 3 parts | 28.57 | Filler |
| | Microcrystalline cellulose 102 | 3 parts | 28.57 | Filler |
| | Hydroxypropyl Cellulose | 1 part | 9.52 | Binder |
| | Silica | 1 part | 9.52 | Glidant |
| | Croscarmellose sodium | 1 part | 9.52 | Disintegrating agent |
| | Magnesium stearate | 0.5 part | 4.76 | Lubricating agent |
| | Gelatin capsule | 1 capsule | 1 capsule | — |
| Formulation 9 | Compound 1 (in terms of $C_{12}H_{19}NO_2 \cdot C_6H_6O_3S$) | 1 part | 1.55 | Active material |
| | Mannitol | 30 parts | 46.51 | Filler |
| | Microcrystalline cellulose 102 | 30 parts | 46.51 | Filler |
| | Hydroxypropyl Cellulose | 1 part | 1.55 | Binder |
| | Silica | 1 part | 1.55 | Glidant |
| | Croscarmellose sodium | 1 part | 1.55 | Disintegrating agent |
| | Magnesium stearate | 0.5 part | 0.78 | Lubricating agent |
| | Gelatin capsule | 1 capsule | 1 capsule | — |

The capsules of Compound 1 as prepared in Example 3 were assayed by high-performance liquid chromatography, according to General Rule 0941 "a test method for content uniformity" in Chinese Pharmacopoeia, 2015 edition. The results are shown in Table 6.

TABLE 6

Uniformity of the capsules of Compound 1

| No. | Value of A + 2.2S | RSD % |
|---|---|---|
| Formulation 4 | 6.25 | 2.53 |
| Formulation 5 | 6.34 | 2.18 |
| Formulation 6 | 4.11 | 1.52 |
| Formulation 7 | 5.48 | 2.45 |
| Formulation 8 | 10.25 | 4.13 |
| Formulation 9 | 12.34 | 4.28 |

The impurity detection was carried out by placing the samples uncovered under a condition of a moisture and heat of 75% RH and 40° C. to measure its impurity content.

The detection results are shown in Table 7.

TABLE 7

The stability of capsules of Compound 1

| | Total impurity/% | | | |
|---|---|---|---|---|
| No. | Day 0 | Day 7 | Day 14 | Day 30 |
| Formulation 4 | 0.054 | 0.153 | 0.284 | 0.573 |
| Formulation 5 | 0.061 | 0.098 | 0.256 | 0.547 |
| Formulation 6 | 0.057 | 0.061 | 0.201 | 0.372 |
| Formulation 7 | 0.059 | 0.139 | 0.372 | 0.781 |

The results show that the impurity levels of Formulations 4-7 were high after 30 days.

Example 4: The Wet Preparation of Capsules of Compound 1

The capsules of Compound 1 were prepared according to the formulations in Table 8 by a preparation method as follows:

(1) subjecting Compound 1 to a 60-mesh sieve, and subjecting mannitol and microcrystalline cellulose to a 40-mesh sieve for use;

(2) formulating a hydroxypropyl cellulose into a 40% aqueous ethanol solution as a binder;

(3) adding Compound 1, mannitol and microcrystalline cellulose into a wet granulator, and adding the binder in (2) thereinto for mixing by shearing to prepare a soft material;

(4) subjecting the soft material to a sieve for producing particles, and then performing static drying;

(5) subjecting the dried soft materials to granulation, and then adding it with croscarmellose sodium and silica in a multi-directional movement mixer for uniform mixing;

(6) adding magnesium stearate in the multi-directional movement mixer for a final mixing;

(7) selecting an appropriate type of capsule and filling the capsule with the mixed powders.

TABLE 8 the raw materials for capsules of Compound 1

| No. | Raw materials | Amount | Weight percentage (%) | Functions |
|---|---|---|---|---|
| Formulation 10 | Compound 1 (in terms of $C_{12}H_{19}NO_2 \cdot C_6H_6O_3S$) | 1 part | 3.92 | Active material |
| | Mannitol | 7 parts | 27.45 | Filler |
| | Microcrystalline cellulose 102 | 14 parts | 54.90 | Filler |
| | Hydroxypropyl Cellulose | 1 part | 3.92 | Binder |
| | Silica | 1 part | 3.92 | Glidant |
| | Croscarmellose sodium | 1 part | 3.92 | Disintegrating agent |
| | Magnesium stearate | 0.5 part | 1.96 | Lubricating agent |
| | Gelatin capsule | 1 capsule | 1 capsule | — |

The capsules of Compound 1 as prepared were assayed by high-performance liquid chromatography, according to General Rule 0941 "a test method for content uniformity" in Chinese Pharmacopoeia, 2015 edition. The results are shown in Table 9.

TABLE 9

Content uniformity of the capsules of Compound 1

| No. | Value of A + 2.2S | RSD % |
|---|---|---|
| Formulation 10 | 5.42 | 2.54 |

Conclusion: the composition as prepared has a value of A+2.2S equal to or less than 15, satisfying the requirement as described in Chinese Pharmacopoeia, 2015 edition for the content uniformity.

The capsule of Compound 1 as prepared was subjected to a dissolution test using high performance liquid chromatography, and the results are shown in Table 10.

TABLE 10 the dissolution of the capsule of Compound 1

| No. | Dissolution rate after 15 mins (%) |
|---|---|
| Formulation 10 | 92.5 |

Conclusion: the composition as prepared can be rapidly dissolved out.

Example 5: The Wet Preparation of Capsules of Compound 1

The capsules of Compound 1 were prepared according to the formulations in Table 11 by a preparation method as follows:

(1) subjecting Compound 1 to a 60-mesh sieve, and subjecting mannitol and microcrystalline cellulose to a 40-mesh sieve for use;
(2) formulating a 40% aqueous ethanol solution as a solvent;
(3) adding Compound 1, hydroxypropyl methyl cellulose, mannitol and microcrystalline cellulose into a wet granulator, and adding the solvent in (2) therein for mixing by shearing to prepare a soft material;
(4) subjecting the soft material to a sieve for producing particles, and then performing dynamic drying on a fluidized bed;
(5) subjecting the dried soft materials to granulation, and then adding it with croscarmellose sodium and silica in a multi-directional movement mixer for uniform mixing;
(6) adding magnesium stearate in the multi-directional movement mixer for a final mixing;
(7) selecting an appropriate type of capsule and filling the capsule with the mixed powders.

TABLE 11 the raw materials for capsules of Compound 1

| No. | Raw materials | Amount | Weight percentage (%) | Functions |
|---|---|---|---|---|
| Formulation 11 | Compound 1 (in terms of $C_{12}H_{19}NO_2 \cdot C_6H_6O_3S$) | 1 part | 3.92 | Active material |
| | Mannitol | 7 parts | 27.45 | Filler |
| | Microcrystalline cellulose 102 | 14 parts | 54.90 | Filler |
| | Hydroxypropyl Cellulose | 1 part | 3.92 | Binder |
| | Silica | 1 part | 3.92 | Glidant |
| | Croscarmellose sodium | 1 part | 3.92 | Disintegrating agent |
| | Magnesium stearate | 0.5 part | 1.96 | Lubricating agent |
| | Gelatin capsule | 1 capsule | 1 capsule | — |

The capsules of Compound 1 as prepared were assayed by high-performance liquid chromatography, according to General Rule 0941 "a test method for content uniformity" in Chinese Pharmacopoeia, 2015 edition. The results are shown in Table 12.

TABLE 12

Content uniformity of the capsules of Compound 1

| No. | Value of A + 2.2S | RSD % |
|---|---|---|
| Formulation 11 | 6.41 | 1.78 |

Conclusion: the composition as prepared has a value of A+2.2S equal to or less than 15, satisfying the requirement as described in Chinese Pharmacopoeia, 2015 edition for the content uniformity.

The capsule of Compound 1 as prepared was subjected to a dissolution test using high performance liquid chromatography, and the results are shown in Table 13.

TABLE 13 the dissolution of the capsule of Compound 1

| No. | Dissolution rate after 15 mins (%) |
|---|---|
| Formulation 11 | 92.4 |

Conclusion: the composition as prepared can be rapidly dissolved out.

The capsules of Compound 1 were prepared according to Table 14 by the method as described in Example 5. The capsules as prepared had a content uniformity satisfying the requirement in Chinese Pharmacopoeia, 2015 edition.

TABLE 14 the raw materials and compositions for capsules of Compound 1

| No. | Actives | Filler 1 | Filler 2 | Binder | Glidant | Disintegrant | Lubricant | Capsule shell |
|---|---|---|---|---|---|---|---|---|
| Formulation 12 | 1 part | Mannitol 30 parts | MCC 30 parts | HPC 1 part | Silica 1 part | CMS 1 part | Magnesium stearate 0.5 part | One Gelatin capsule |
| Formulation 13 | 1 part | Mannitol 7 parts | MCC 14 parts | HPC 1 part | Silica 1 part | CMS 1 part | Magnesium stearate 0.5 part | One Gelatin capsule |
| Formulation 14 | 1 part | Mannitol 7 parts | MCC 14 parts | HPC 1 part | Silica 1 part | CMSS 1 part | Magnesium stearate 0.5 part | One Gelatin capsule |
| Formulation 15 | 1 part | Mannitol 7 parts | MCC 14 parts | HPC 0.1 part | Silica 1 part | CMS 1 part | Magnesium stearate 0.5 part | One Gelatin capsule |
| Formulation 16 | 1 part | Mannitol 7 parts | MCC 14 parts | HPC 3 parts | Silica 1 part | CMS 1 part | Magnesium stearate 0.5 part | One Gelatin capsule |
| Formulation 17 | 1 part | Mannitol 7 parts | MCC 14 parts | HPMC 0.1 part | Silica 1 part | CMS 1 part | Magnesium stearate 0.5 part | One Gelatin capsule |
| Formulation 18 | 1 part | Mannitol 7 parts | MCC 14 parts | HPMC 3 parts | Silica 1 part | CMS 1 part | Magnesium stearate 0.5 part | One Gelatin capsule |
| Formulation 19 | 1 part | Mannitol 7 parts | MCC 14 parts | Povidone 0.1 part | Silica 1 part | CMS 1 part | Magnesium stearate 0.5 part | One Gelatin capsule |
| Formulation 20 | 1 part | Mannitol 7 parts | MCC 14 parts | Povidone 5 parts | Silica 1 part | CMS 1 part | Magnesium stearate 0.5 part | One Gelatin capsule |
| Formulation 21 | 1 part | Mannitol 7 parts | MCC 14 parts | HPC 1 part | Silica 5 parts | CMS 1 part | Magnesium stearate 0.5 part | One Gelatin capsule |
| Formulation 22 | 1 part | Mannitol 7 parts | MCC 14 parts | HPC 1 part | Talc 1 part | CMS 1 part | Magnesium stearate 0.5 part | One Gelatin capsule |
| Formulation 23 | 1 part | Mannitol 7 parts | MCC 14 parts | HPC 1 part | Talc 5 parts | CMS 1 part | Magnesium stearate 0.5 part | One Gelatin capsule |
| Formulation 24 | 1 part | Mannitol 7 parts | MCC 14 parts | HPC 1 part | Silica 1 part | CMS 1 part | Magnesium stearate 2 份 | One Gelatin capsule |
| Formulation 25 | 1 part | Mannitol 7 parts | MCC 14 parts | HPC 1 part | Silica 1 part | CMS 1 part | Magnesium stearate 0.1 part | One Gelatin capsule |
| Formulation 26 | 1 part | Mannitol 7 parts | MCC 14 parts | HPC 1 part | Silica 1 part | CMS 1 part | Stearic acid 2 parts | One Gelatin capsule |
| Formulation 27 | 1 part | Mannitol 7 parts | MCC 14 parts | HPC 1 part | Silica 1 part | CMS 1 part | Stearic acid 0.1 part | One Gelatin capsule |
| Formulation 28 | 1 part | Mannitol 7 parts | MCC 14 parts | HPC 1 part | Silica 1 part | CMS 1 part | SSF 2 parts | One Gelatin capsule |

TABLE 14-continued the raw materials and compositions for capsules of Compound 1

| No. | Actives | Filler 1 | Filler 2 | Binder | Glidant | Disintegrant | Lubricant | Capsule shell |
|---|---|---|---|---|---|---|---|---|
| Formulation 29 | 1 part | Mannitol 7 parts | MCC 14 parts | HPC 1 part | Silica 1 part | CMS 1 part | SSF 0.1 part | One Gelatin capsule |
| Formulation 30 | 1 part | Mannitol 7 parts | MCC 14 parts | HPC 1 part | Silica 1 part | CMS 1 part | Glyceryl Behenate 2 parts | One Gelatin capsule |
| Formulation 31 | 1 part | Mannitol 7 parts | MCC 14 parts | HPC 1 part | Silica 1 part | CMS 1 part | Glyceryl Behenate 0.1 part | One Gelatin capsule |
| Formulation 32 | 1 part | Mannitol 7 parts | MCC 14 parts | HPC 1 part | Silica 1 part | CMS 1 part | Magnesium stearate 0.5 part | One blank HPS capsule |
| Formulation 33 | 1 part | Mannitol 7 parts | MCC 14 parts | HPC 1 part | Silica 1 part | CMS 1 part | Magnesium stearate 0.5 part | One HPMC capsule |

The abbreviations in the above table:
MCC: Microcrystalline cellulose
HPC: Hydroxypropyl cellulose
HPMC: Hydroxypropyl methyl cellulose
CMS: Croscarmellose sodium
HPS: Hydroxypropyl starch Example 6: Capsules of Compound 1

The capsules of Compound 1 were prepared according to the formulations in Table 15 by a preparation method as follows:
(1) subjecting a bulk drug of Compound 1 to a 60-mesh sieve, and subjecting the filler to a 40-mesh sieve for use;
(2) adding the Compound 1 and the filler in a multi-directional movement mixer for uniform mixing;
(3) adding a lubricating agent and other additives in the multi-directional movement mixer for a final mixing with the mixture in (2);
(4) filling a capsule with the mixed powders.

TABLE 15 the raw materials and compositions for capsules of Compound 1

| No. | Raw materials | Amount | Weight percentage (%) | Functions |
|---|---|---|---|---|
| Formulation 34 | Compound 1 (in terms of $C_{12}H_{19}NO_2 \cdot C_6H_6O_3S$) | 1 part | 5.52 | — |
| | Mannitol | 17 parts | 93.92 | Filler |
| | Magnesium stearate | 0.1 part | 0.55 | Lubricating agent |
| | Gelatin blank capsule | 1 capsule | 1 capsule | — |
| Formulation 35 | Compound 1 (in terms of $C_{12}H_{19}NO_2 \cdot C_6H_6O_3S$) | 1 part | 5.52 | — |
| | Microcrystalline cellulose 102 | 17 parts | 93.92 | Filler |
| | Magnesium stearate | 0.1 part | 0.55 | Lubricating agent |
| | Gelatin blank capsule | 1 capsule | 1 capsule | — |
| Formulation 36 | Compound 1 (in terms of $C_{12}H_{19}NO_2 \cdot C_6H_6O_3S$) | 1 part | 6.06 | — |
| | Mannitol | 5 parts | 30.30 | Filler |
| | Microcrystalline cellulose 102 | 10 parts | 62.11 | Filler |
| | Magnesium stearate | 0.1 part | 0.62 | Lubricating agent |
| | Gelatin blank capsule | 1 capsule | 1 capsule | — |

The capsules of Compound 1 as prepared were assayed by high-performance liquid chromatography, according to General Rule 0941 "a test method for content uniformity" in Chinese Pharmacopoeia, 2015 edition. The results are shown in Table 16.

TABLE 16

Content uniformity of the capsules of Compound 1

| No. | Value of A + 2.2S of Capsules | RSD % of mixed powders |
|---|---|---|
| Formulation 34 | 18.9 | 9.64 |
| Formulation 35 | 21.4 | 12.5 |
| Formulation 36 | 15.4 | 6.24 |

Conclusion: the formulations 34, 35 and 36 have a value of A+2.2S larger than 15, which does not satisfy the requirement as described in Chinese Pharmacopoeia, 2015 edition for the content uniformity.

Example 7: Capsules of Compound 1

The capsules of Compound 1 were prepared according to the formulations in Table 17 by a preparation method as follows:

(1) subjecting a bulk drug of Compound 1 to a 60-mesh sieve, and subjecting the filler to a 40-mesh sieve for use;

(2) adding the Compound 1 and the filler in a multi-directional movement mixer for uniform mixing;

(3) adding a lubricating agent and other additives in the multi-directional movement mixer for a final mixing with the mixture in (2);

(4) filling a capsule with the mixed powders.

TABLE 17 the raw materials and compositions for capsules of Compound 1

| No. | Raw materials | Amount | Weight percentage (%) | Functions |
|---|---|---|---|---|
| Formulation 37 | Compound 1 (in terms of $C_{12}H_{19}NO_2 \cdot C_6H_6O_3S$) | 1 part | 5.85 | — |
|  | Mannitol | 5 parts | 29.24 | Filler |
|  | Microcrystalline cellulose 102 | 10 parts | 58.48 | Filler |
|  | Hydroxypropyl cellulose | 1 part | 5.85 | Binder |
|  | Magnesium stearate | 0.1 part | 0.58 | Lubricating agent |
|  | Gelatin blank capsule | 1 capsule | 1 capsule | — |
| Formulation 38 | Compound 1 (in terms of $C_{12}H_{19}NO_2 \cdot C_6H_6O_3S$) | 1 part | 5.85 | — |
|  | Mannitol | 5 parts | 29.24 | Filler |
|  | Microcrystalline cellulose 102 | 5 parts | 29.24 | Filler |
|  | Microcrystalline cellulose 101 | 5 parts | 29.24 | Filler |
|  | Hydroxypropyl cellulose | 1 part | 5.85 | Binder |
|  | Magnesium stearate | 0.1 part | 0.58 | Lubricating agent |
|  | Gelatin blank capsule | 1 capsule | 1 capsule | — |

Impurity test: the sample was placed under a condition of a moisture of 75% RH and 40° C. (uncovered) for its impurity test. The variations of a total impurity content are shown in Table 18.

TABLE 18

Variations of a total impurity content in capsules of Compound 1

| Sample No. | Total impurity/% | | | |
|---|---|---|---|---|
| | Day 0 | Day 7 | Day 14 | Day 30 |
| Formulation 37 | 0.051 | 0.065 | 0.148 | 0.342 |
| Formulation 38 | 0.054 | 0.066 | 0.164 | 0.387 |

The capsules of Compound 1 as prepared were assayed by high-performance liquid chromatography, according to General Rule 0941 "a test method for content uniformity" in Chinese Pharmacopoeia, 2015 edition. The results are shown in Table 19.

TABLE 19

Content uniformity of the capsules of Compound 1

| No. | Value of A + 2.2S of Capsules | RSD % of mixed powders |
|---|---|---|
| Formulation 37 | 10.5 | 5.44 |
| Formulation 38 | 8.42 | 4.29 |

It can be seen from the above results that the compatibility of the active material and excipients was improved.

Example 8: Capsules of Compound 1

The capsules of Compound 1 were prepared according to the formulations in Table 20 by a preparation method as follows:
(1) subjecting a bulk drug of Compound 1 to a 60-mesh sieve, and subjecting the filler to a 40-mesh sieve for use;
(2) adding the Compound 1 and the filler in a multi-directional movement mixer for uniform mixing;
(3) adding a lubricating agent and other additives in the multi-directional movement mixer for a final mixing with the mixture in (2);
(4) filling a capsule with the mixed powders.

TABLE 20 the raw materials and compositions for capsules of Compound 1

| No. | Raw materials | Amount | Weight percentage (%) | Functions |
|---|---|---|---|---|
| Formulation 39 | Compound 1 (in terms of $C_{12}H_{19}NO_2 \cdot C_6H_6O_3S$) | 1 part | 6.21 | — |
| | Mannitol | 5 parts | 31.06 | Filler |
| | Microcrystalline cellulose 102 | 5 parts | 31.06 | Filler |
| | Microcrystalline cellulose 103 | 5 parts | 31.06 | Filler |
| | Magnesium stearate | 0.1 part | 0.62 | Lubricating agent |
| | Gelatin blank capsule | 1 capsule | 1 capsule | — |
| Formulation 40 | Compound 1 (in terms of $C_{12}H_{19}NO_2 \cdot C_6H_6O_3S$) | 1 part | 6.21 | — |
| | Mannitol | 5 parts | 31.06 | Filler |
| | Microcrystalline cellulose 102 | 5 part | 31.06 | Filler |
| | Microcrystalline cellulose 112 | 5 parts | 31.06 | Filler |
| | Magnesium stearate | 0.1 part | 0.62 | Lubricating agent |
| | Gelatin blank capsule | 1 capsule | 1 capsule | — |

TABLE 20-continued the raw materials and compositions for capsules of Compound 1

| No. | Raw materials | Amount | Weight percentage (%) | Functions |
|---|---|---|---|---|
| Formulation 41 | Compound 1 (in terms of $C_{12}H_{19}NO_2 \cdot C_6H_6O_3S$) | 1 part | 6.21 | — |
| | Mannitol | 5 parts | 31.06 | Filler |
| | Microcrystalline cellulose 102 | 5 parts | 31.06 | Filler |
| | Microcrystalline cellulose 14 | 5 parts | 31.06 | Filler |
| | Magnesium stearate | 0.1 part | 0.62 | Lubricating agent |
| | Gelatin blank capsule | 1 capsule | 1 capsule | — |
| Formulation 42 | Compound 1 (in terms of $C_{12}H_{19}NO_2 \cdot C_6H_6O_3S$) | 1 part | 6.21 | — |
| | Mannitol | 5 parts | 31.06 | Filler |
| | Microcrystalline cellulose 102 | 5 parts | 31.06 | Filler |
| | Microcrystalline cellulose 12 | 5 parts | 31.06 | Filler |
| | Magnesium stearate | 0.1 part | 0.62 | Lubricating agent |
| | Gelatin blank capsule | 1 capsule | 1 capsule | — |
| Formulation 43 | Compound 1 (in terms of $C_{12}H_{19}NO_2 \cdot C_6H_6O_3S$) | 8 parts | 44.2 | — |
| | Microcrystalline cellulose 102 | 7.6 parts | 41.99 | Filler |
| | Microcrystalline cellulose 12 | 0.6 part | 3.31 | Filler |
| | Mannitol | 1.8 parts | 9.94 | Filler |
| | Magnesium stearate | 0.1 part | 0.55 | Lubricating agent |
| | Gelatin blank capsule | 1 capsule | | — |
| Formulation 44 | Compound 1 (in terms of $C_{12}H_{19}NO_2 \cdot C_6H_6O_3S$) | 1 part | 5.85 | — |
| | Microcrystalline cellulose 102 | 3 parts | 17.54 | Filler |
| | Microcrystalline cellulose 12 | 10 parts | 58.48 | Filler |
| | Mannitol | 3 parts | 17.54 | Filler |
| | Magnesium stearate | 0.1 part | 0.58 | Lubricating agent |
| | Gelatin blank capsule | 1 capsule | | — |
| Formulation 45 | Compound 1 (in terms of $C_{12}H_{19}NO_2 \cdot C_6H_6O_3S$) | 1 part | 5.26 | — |
| | Microcrystalline cellulose 102 | 13 parts | 68.42 | Filler |
| | Microcrystalline cellulose 12 | 1 part | 5.26 | Filler |
| | Mannitol | 3 part | 15.79 | Filler |
| | Magnesium stearate | 1 part | 5.26 | Lubricating agent |
| | Gelatin blank capsule | 1 capsule | | — |

The capsules of Compound 1 as prepared were assayed by high-performance liquid chromatography, according to General Rule 0941 "a test method for content uniformity" in Chinese Pharmacopoeia, 2015 edition. The results are shown in Table 21.

TABLE 21

Content uniformity of the capsules of Compound 1

| No. | Value of A + 2.2S of Capsules | RSD % of mixed powders |
|---|---|---|
| Formulation 39 | 15.3 | 8.47 |
| Formulation 40 | 11.4 | 7.58 |
| Formulation 41 | 10.7 | 7.4 |
| Formulation 42 | 8.5 | 5.18 |
| Formulation 43 | 4.67 | 1.21 |
| Formulation 44 | 6.27 | 2.87 |
| Formulation 45 | 7.24 | 0.97 |

Conclusion: the formulation 39 has a value of A+2.2S larger than 15, which does not satisfy the requirement as described in Chinese Pharmacopoeia, 2015 edition for the content uniformity. The formulations 42, 43, 44 and 45 were improved in the content uniformity.

Example 9: The Preparation of Capsule Formulations of Specification of 5 mg and 20 mg of an Active Material (in Terms of Free Base of Compound 1)

The capsules of Compound 1 were prepared according to the formulations in Table 22 by a preparation method as follows:

(1) subjecting a bulk drug of Compound 1 to a 60-mesh sieve, and subjecting the filler to a 40-mesh sieve for use;

(2) adding the Compound 1 and the filler in a multi-directional movement mixer for uniform mixing;

(3) adding a lubricating agent in the multi-directional movement mixer for a final mixing with the mixture in (2);

(4) filling a capsule with the mixed powders.

TABLE 22 the compositions for capsules of Compound 1

| No. | Raw materials | Amount | Weight percentage (%) | Functions |
|---|---|---|---|---|
| Formulation 46 (5 mg) | Compound 1 (in terms of $C_{12}H_{19}NO_2 \cdot C_6H_6O_3S$) | 1 part | 5.52 | Active material |
| | Microcrystalline cellulose 102 | 13 parts | 71.82 | Filler |
| | Microcrystalline cellulose 12 | 1 part | 5.52 | Filler |
| | Mannitol | 3 parts | 16.57 | Filler |
| | Magnesium stearate | 0.1 part | 0.55 | Lubricating agent |
| | Gelatin blank capsule | 1 capsule | 1 capsule | — |
| Formulation 47 (5 mg) | Compound 1 (in terms of $C_{12}H_{19}NO_2 \cdot C_6H_6O_3S$) | 1 part | 5.52 | Active material |
| | Microcrystalline cellulose 102 | 11 parts | 60.77 | Filler |
| | Microcrystalline cellulose 12 | 1 part | 5.52 | Filler |
| | Mannitol | 5 parts | 27.62 | Filler |
| | Magnesium stearate | 0.1 part | 0.55 | Lubricating agent |
| | Gelatin blank capsule | 1 capsule | 1 capsule | — |
| Formulation 48 (20 mg) | Compound 1 (in terms of $C_{12}H_{19}NO_2 \cdot C_6H_6O_3S$) | 4 parts | 20.41 | Active material |
| | Microcrystalline cellulose 102 | 11 parts | 56.12 | Filler |
| | Microcrystalline cellulose 12 | 1.5 parts | 7.65 | Filler |
| | Mannitol | 3 parts | 15.31 | Filler |
| | Magnesium stearate | 0.1 part | 0.51 | Lubricating agent |
| | Gelatin blank capsule | 1 capsule | 1 capsule | — |

The capsules of Compound 1 as prepared were assayed by high-performance liquid chromatography, according to General Rule 0941 "a test method for content uniformity" in Chinese Pharmacopoeia, 2015 edition. The results are shown in Table 23.

TABLE 23

Content uniformity of the capsules of Compound 1

| No. | Value of A + 2.2S | RSD % |
|---|---|---|
| Formulation 46 | 3.52 | 1.09 |
| Formulation 47 | 3.21 | 0.86 |
| Formulation 48 | 3.18 | 0.94 |

It can be seen from the test results that the formulations 46 to 48 were improved in the content uniformity.

The capsules of Compound 1 as prepared were also subjected to a dissolution test by high performance liquid chromatography, and the test results are shown in Table 24.

TABLE 24

Dissolution of capsules of Compound 1

| | Dissolution rate % Month 0 | | | | | |
|---|---|---|---|---|---|---|
| No. | 3 mins | 5 mins | 10 mins | 15 mins | 20 mins | 30 mins |
| Formulation 46 | 66.24 | 91.21 | 99.81 | 100.03 | 101.08 | 101.15 |
| Formulation 47 | 64.69 | 90.69 | 99.65 | 101.21 | 102.17 | 102.89 |
| Formulation 48 | 71.30 | 90.29 | 96.46 | 98.30 | 98.98 | 99.06 |

It can be seen from the test results that the compositions as prepared can all dissolved out rapidly.

Example 10: Study on Stability

Objectives: to perform study on the stability for formulations 47 and 48.

Method: the capsules of formulations 47 and 48 were packed by a luminium foil and a solid composite plate of polyvinyl chloride/polyethylene/polyvinylidene chloride for medicine, placed uncovered under the conditions of 75% RH and 40° C. for 1 month, and then measured for its impurity content, active material content (equal to a ratio of the active material content as tested to the active material content as marked, by using a mark content as reference) and dissolution speed. The result is shown in Tables 25-27.

TABLE 25

Variations in total impurity content

| | Total impurity content(%) | | |
|---|---|---|---|
| No. | 1 month | 3 months | 6 months |
| Formulation 47 | 0.121 | 0.153 | 0.237 |
| Formulation 48 | 0.117 | 0.136 | 0.197 |

TABLE 26

Variations in the content

| | Content, % (compared to the mark content) | | |
|---|---|---|---|
| No. | 1 month | 3 months | 6 months |
| Formulation 47 | 100.57 | 100.16 | 99.98 |
| Formulation 48 | 100.86 | 100.06 | 100.05 |

TABLE 27

| | Dissolution | | |
|---|---|---|---|
| | Dissolution rate after 15 mins (%) | | |
| No. | 1 month | 3 months | 6 months |
| Formulation 47 | 99.74 | 99.12 | 98.31 |
| Formulation 48 | 98.28 | 98.21 | 98.09 |

Example 11: Tablets of Compound 1 with Various Specification

The tablets of Compound 1 with various specification (in terms of free base of Compound 1) are prepared according to the composition in Table 28.

TABLE 28 the composition of tablets of Compound 1

| No. | Raw materials | Amount (mg) | Functions |
|---|---|---|---|
| Formulation 49 (15 mg) | Compound 1 (in terms of $C_{12}H_{19}NO_2 \cdot C_6H_6O_3S$) | 26.34 | — |
| | Mannitol | 42.31 | Filler |
| | Microcrystalline cellulose | 126.91 | Filler |
| | Hydroxypropyl methyl cellulose | 15.00 | Binder |
| | Croscarmellose sodium | 20.00 | Disintegrating agent |
| | Magnesium stearate | 2.00 | Lubricating agent |
| Formulation 50 (30 mg) | Compound 1 (in terms of $C_{12}H_{19}NO_2 \cdot C_6H_6O_3S$) | 52.68 | — |
| | Mannitol | 42.31 | Filler |
| | Microcrystalline cellulose | 126.91 | Filler |
| | Hydroxypropyl methyl cellulose | 15.00 | Binder |
| | Croscarmellose sodium | 20.00 | Disintegrating agent |
| | Magnesium stearate | 2.00 | Lubricating agent |
| Formulation 51 (60 mg) | Compound 1 (in terms of $C_{12}H_{19}NO_2 \cdot C_6H_6O_3S$) | 105.36 | — |
| | Mannitol | 42.31 | Filler |
| | Microcrystalline cellulose | 126.91 | Filler |
| | Hydroxypropyl methyl cellulose | 15.00 | Binder |
| | Croscarmellose sodium | 20.00 | Disintegrating agent |
| | Magnesium stearate | 2.00 | Lubricating agent |
| Formulation 52 (5 mg) | Compound 1 (in terms of $C_{12}H_{19}NO_2 \cdot C_6H_6O_3S$) | 8.78 | Active material |
| | Microcrystalline cellulose 102 | 114.14 | Filler |
| | Microcrystalline cellulose 12 | 8.78 | Filler |
| | Mannitol | 26.34 | Filler |
| | Magnesium stearate | 0.88 | Lubricating agent |
| Formulation 53 (5 mg) | Compound 1 (in terms of $C_{12}H_{19}NO_2 \cdot C_6H_6O_3S$) | 8.78 | Active material |
| | Microcrystalline cellulose 102 | 96.58 | Filler |
| | Microcrystalline cellulose 12 | 8.78 | Filler |
| | Mannitol | 43.9 | Filler |
| | Magnesium stearate | 0.88 | Lubricating agent |
| Formulation 54 (20 mg) | Compound 1 (in terms of $C_{12}H_{19}NO_2 \cdot C_6H_6O_3S$) | 35.12 | Active material |
| | Microcrystalline cellulose 102 | 96.58 | Filler |
| | Microcrystalline cellulose 12 | 13.17 | Filler |
| | Mannitol | 26.34 | Filler |
| | Magnesium stearate | 0.88 | Lubricating agent |

The preparation method is as follows:
(1) subjecting an active drug of Compound 1 to a 100-mesh sieve, and subjecting the filler and disintegrating agent to a 60-mesh sieve for use;
(2) adding the active drug of Compound 1, the filler and the disintegrating agent into a high-speed wet granulator for uniform mixing;
(3) adding a prescribed amount of a solution of hydroxypropyl methyl cellulose as a binder to prepare a soft material;
(4) subjecting the soft material to a 20-mesh sieve for producing particles;
(5) subjecting the particles as produced to dynamic drying on a fluidized bed to adjust the moisture content to be less than 2%;
(6) subjecting the dried particles to a 24-mesh sieve for granulating;
(7) adding the granules with a prescribed amount of magnesium stearate into a multi-directional movement mixer for uniform mixing; and
(8) press-molding the final mixed powders with a mould having a proper size into tablets.

Example 12: The Stability Test

The tablets in formulations 49 to 54 were placed uncovered under the conditions of a temperature of 40° C.±2° C., and a relative humidity of 75%±5%, respectively. Then, they were tested on day 7, day 14 and day 30 for the relevant materials. The test results are shown in Table 29.

TABLE 29 test results of relevant materials

| Examples | Day 0 | Day 7 | Day 14 | Day 30 |
| --- | --- | --- | --- | --- |
| | Numbers of impurities | | | |
| Formulation 49 | 4 | 5 | 5 | 8 |
| Formulation 50 | 5 | 5 | 5 | 8 |
| Formulation 51 | 5 | 5 | 5 | 8 |
| Formulation 52 | 3 | 4 | 4 | 5 |
| Formulation 53 | 3 | 4 | 4 | 4 |
| Formulation 54 | 3 | 4 | 5 | 6 |
| | Total impurity content (%) | | | |
| Formulation 49 | 0.037 | 0.056 | 0.060 | 0.085 |
| Formulation 50 | 0.061 | 0.066 | 0.097 | 0.120 |
| Formulation 51 | 0.054 | 0.055 | 0.064 | 0.173 |
| Formulation 52 | 0.039 | 0.048 | 0.051 | 0.073 |
| Formulation 53 | 0.036 | 0.048 | 0.054 | 0.087 |
| Formulation 54 | 0.040 | 0.052 | 0.060 | 0.085 |

Conclusion: it can be seen from the test results that impurities increase of formulations 49~54 are not significant and the formulations are relatively stable.

Example 13: The Preparation of Tablets by One-Step Method

The formulations 49-2, 50-2 and 51-2 were respectively produced by using a top spray process on a fluidized bed, according to the compositions of formulations 49, 50 and 51.
The method for preparing tablets by one-step method is as follows:
(1) subjecting an active drug of Compound 1 to a 100-mesh sieve, and subjecting the filler and disintegrating agent to a 60-mesh sieve for use;
(2) adding the active drug of Compound 1, the filler and the disintegrating agent into a multi-directional movement mixer for uniform mixing;
(3) adding the mixed powder to a fluidized bed, pumping a solution of hydroxypropyl methyl cellulose into the fluidized bed with a peristaltic pump, and producing particles by top spray, wherein the inlet temperature is set to 60° C. to 65° C., the material temperature is controlled to 30° C. to 35° C., the air feeding rate is set to 140 m³/h to 180 m³/h, and the peristaltic pump is controlled to 20 rpm to 80 rpm;
(4) subjecting the dried particles to a 24-mesh sieve for granulating;
(5) adding the granules with magnesium stearate into a multi-directional movement mixer for uniform mixing; and
(6) press-molding the final mixed powders with a mould having a proper size into tablets.

The tablets in formulations 49-2, 50-2 and 51-2 were placed uncovered under the conditions of a temperature of 40° C.±2° C., and a relative humidity of 75%±5%, respectively. Then, they were tested on day 7, day 14 and day 30 for the relevant materials. The test results are shown in Table 30.

TABLE 30 test results of relevant materials

| No. | Day 0 | Day 7 | Day 14 | Day 30 |
| --- | --- | --- | --- | --- |
| | Numbers of impurities | | | |
| Formulation 49-2 | 4 | 5 | 5 | 8 |
| Formulation 50-2 | 5 | 5 | 5 | 8 |
| Formulation 51-2 | 5 | 5 | 5 | 8 |
| | Total impurity content (%) | | | |
| Formulation 49-2 | 0.036 | 0.055 | 0.060 | 0.084 |
| Formulation 50-2 | 0.060 | 0.064 | 0.095 | 0.120 |
| Formulation 51-2 | 0.053 | 0.054 | 0.064 | 0.172 |

Conclusion: it can be seen from the test results that impurities increase of formulations 54-2, 56-2 and 62-2 are not significant and the tablets are relatively stable. Meanwhile, compared with tablets obtained by a high-efficiency wet granulation process, the impurity content has no obvious difference.

Example 14: Bioassay

1. Test on the Competitive Binding Ability of Compounds to the Calcium-Ion Channel Protein Cavα2δ

A rat cerebral cortex tissue was placed in an ice-cold 0.32M sucrose/5 mM Tris-acetic acid (pH 7.4) having a 10-folded volume, and subjected to a sucrose density gradient centrifugation to prepare synaptic plasma membrane, which was stored in a Tris-acetic acid (pH 7.4) buffer, and re-suspended in a 10 mM HEPES (pH 7.4) buffer prior to use. The test compound was dissolved in 1% DMSO and diluted to a gradient concentration (1 nM-1000 nM), added to the suspension of synaptic plasma membrane (having about 0.05-0.1 mg protein in total) with 20 nM [3H] gabapentin and incubated at 25° C. for 30 mins. At the end of the reaction, the system was vacuum filtered into Whatman GFB membranes, which were washed three times with 5 mL of 100 mM ice-cold sodium chloride. The radioactivity of the membranes were measured by a liquid scintillation counter. Non-specific binding was closed with 100 mM gabapentin.

The inhibition rate of the compound on the binding of radiolabeled gabapentin to the synaptic plasma membrane was calculated and the IC50 of the compound was also calculated. IC50 for Compound 1 is 3.96 nM. Compound 1 has a good competitive binding capacity to the calcium-ion channel protein Cavα2δ.

2. Animal Models of L5-L6 Spinal Nerve Ligation (SNL)

Six- to seven-week-old SD male rats (from Charles River) were anesthetized with 5% isoflurane in an animal surgical setting. The anesthetized animals were placed in prone position, incised at the 5th lumbar vertebra. The skin was opened to expose the left paravertebral muscles, and the L5 and L6 spinal nerves were exposed by laceration layer by layer. 4-0 surgical wires were used to ligate the distal ends of the L5 and L6 dorsal root ganglia. The muscles and skin were sutured layer by layer, and the animals were left recovered for one week.

After recovery, the model animals were tested for contact pain using a Von Frey wire (DanMic Global, USA). The "up-down" method was used to measure the strength of the animal having 50% leg retraction response (g; 50% PWT). First, animals were grouped with a 50% PWT of 1-5 g. Before administration, animals were tested for base value, followed by oral administration of different compounds (formulated with 5% sodium carboxymethyl cellulose). The animals were tested for pain responses at different timing for the test range of 1.0 g to 15 g. The test results are shown in FIG. 1.

Conclusion: The compounds according to the present disclosure can significantly inhibit the mechanical pain hypersensitivity caused by spinal nerve ligation in rats.

3. Rat CCI-Induced Nociception Sensitization Model

SD rats of 160-180 g were purchased from Charles River (Beijing) with a license number of sCXK (Beijing)-2012-001 and a qualification number of 11400700254251. The surgery was performed to establish the CCI model as follows: the animals ware first anesthetized, then the left posterior sciatic nerve was exposed. A 2 mm long PE-90 catheter was applied to the middle site of the sciatic nerve. Finally the muscle and skin were sutured. Adaptation of the animal's left hind limb at 15g was carried out from day 10 after the surgery, three times a week.

The baseline testing was performed 17 days after surgery (starting from 2g at the time of testing, with an upper limit of 8g and a lower limit of 1g which is the −24h point), with a pain threshold of 1-4g as a grouping criterion. Grouping was done according to baseline test results, with 10 animals per group. The animals in the group were fasted but given water overnight. On the second day, mechanical pain values were tested at 2 h, 4 h and 6 h after oral/intragastric administration. The test started at 8 g, with an upper limit of 15g and a lower limit of 1g.

The data were processed according to equation (1) to calculate the PWT 50% value, where Xf is the log value of the final test fibers used in the test, k is a table value (Chaplan et al., 1994), and δ is the mean difference (here 0.224).

$$PWT50\%(g) = (10[Xf + k\delta])/10000 \quad \text{[equation (1)]}$$

The data were expressed in a form of mean±standard deviation (X±s) and were statistically analyzed using one-way ANOVA and Dunnett's t test (Graphpad prism 6.01).

Figure 2:
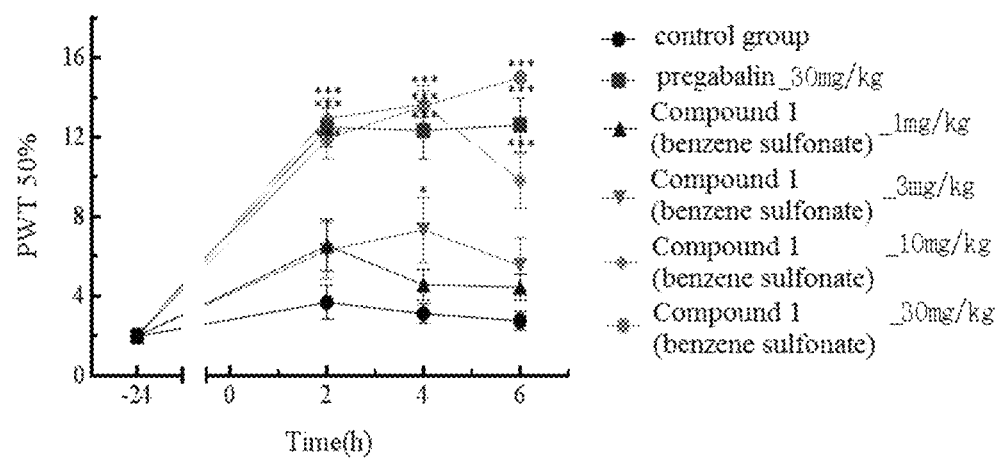
FIG. 2 is graph showing the effect on the mechanical pain threshold value after single-dose of Compound 1 is administrated to CCI modeling rat (X±s, n=10)
Figure 3:
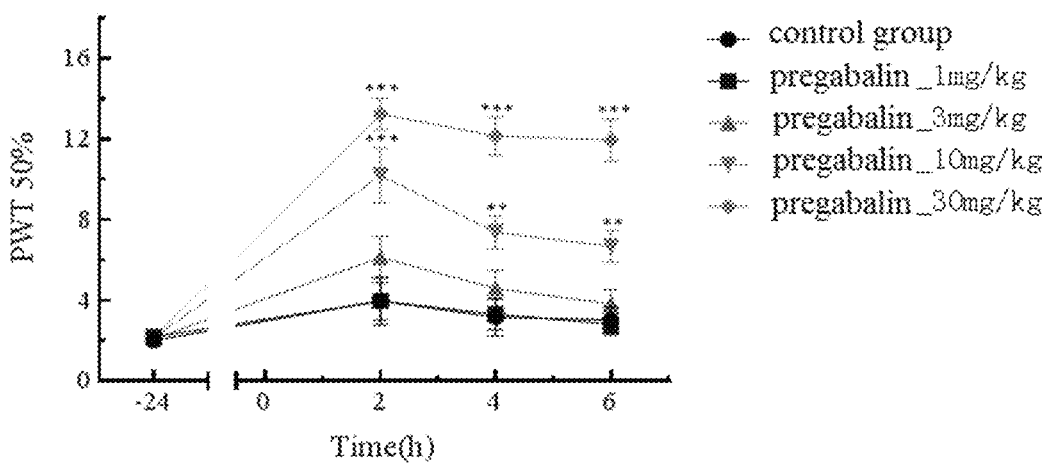
FIG. 3 is graph showing the effect on the mechanical pain threshold value after single-dose of Pregabalin is administrated to CCI modeling rat (X±s, n=10)

The experimental results are shown in FIGS. 2 and 3, which show that the mechanical pain threshold of CCI molded SD rats was significantly increased after single oral administration of Compound 1 and pregabalin. Compound 1 has an effective dose of 3 mg/kg, which is superior to pregabalin having an effective dose of 10 mg/kg.

Although specific embodiments of the disclosure have been described, those skilled in the art should recognize that a variety of changes and modifications can be made to the disclosure without departing from the scope or spirit of the disclosure. Thus, the present disclosure is intended to cover all such alterations and modifications that fall within the scope defined in the appended claims and their equivalents.

What claimed is:

1. A pharmaceutical composition in a form of capsule or tablet comprising:
   (i) an active material having a structure as represented by formula (I) or a pharmaceutically acceptable salt in an amount of 5% to 45% by weight;
   (ii) one or more filler; wherein the filler is a combination of mannitol with a content of 10% to 28% by weight, microcrystalline cellulose A with a content of 3% to 8% by weight and microcrystalline cellulose B with a content of 40% to 75% by weight; wherein, the microcrystalline cellulose A is microcrystalline cellulose 12; the microcrystalline cellulose B is microcrystalline celluloses of 102; and
   (iii) one or more lubricating agents in an amount of 0.5% to 5.5% by weight; wherein the lubricating agent is magnesium stearate;
   wherein the sum of weight percentages of all the components is 100%;
   wherein the structure of formula (I) is as follows:

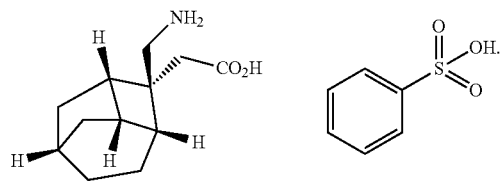 [SMILES: NC[C@@]1(CC(=O)O)[C@@H]2CC[C@H]3C[C@@H]2[C@@H]1C3 ; O=S(=O)(O)c1ccccc1]

2. The composition according to claim 1, wherein the active material is included in an amount of 5% to 35% by weight.

3. The composition according to claim 1, wherein the active material is included in an amount of 21% to 40% by weight.

4. The composition according to claim 1, wherein the lubricating agent is included in an amount of 0.5% to 2% by weight.

5. The composition according to claim 1, comprising, one or more binders which are selected from hydroxypropyl cellulose or povidone.

6. The composition according to claim 1, comprising, one or more disintegrating agents which are selected from croscarmellose sodium or sodium carboxymethyl starch.

7. The composition according to claim 1, comprising, one or more glidants which are selected from silica or talc.

8. The composition according to claim 1, comprising:
   (i) a pharmaceutically acceptable salt of the compound of formula (I), as an active material, which is included in an amount of 5% to 21% by weight;
   (ii) a filler comprising mannitol, microcrystalline cellulose A and microcrystalline cellulose B, wherein mannitol is included in an amount of 15% to 28% by weight, the microcrystalline cellulose A is included in an amount of 5% to 8% by weight, and the microcrystalline cellulose B is included in an amount of 56% to 61% by weight; and (iii) magnesium stearate which is included in an amount of 0.5% to 0.6% by weight;

wherein the total percentage of all components is 100%; and wherein the pharmaceutically acceptable salt of the compound of formula (I) has a structure as follows:

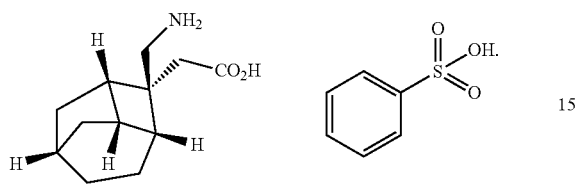

9. The composition according to claim 8, wherein the composition comprises a glidant selected from silica or talc and/or a binder selected from hydroxypropyl cellulose.

10. The composition according to claim 1, wherein the active material is present, in terms of a free base thereof, in an amount of 1 to 100 mg.

11. The composition according to claim 1, wherein the active material is present, in terms of a free base thereof, in an amount of 5 mg, 20 mg, 30 mg, 40 mg, 60 mg, or 80 mg.

* * * * *